US006734336B1

(12) United States Patent
Scott et al.

(10) Patent No.: US 6,734,336 B1
(45) Date of Patent: *May 11, 2004

(54) GENE-TARGETED NON-HUMAN MAMMAL WITH HUMAN FAD PRESENILIN MUTATION AND GENERATIONAL OFFSPRING

(75) Inventors: Richard W. Scott, West Chester, PA (US); Andrew G. Reaume, Waterford, CT (US); Karen Dorfman, Waterford, CT (US)

(73) Assignee: Cephalon, Inc., West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/621,897

(22) Filed: Jul. 20, 2000

Related U.S. Application Data

(63) Continuation-in-part of application No. 09/041,185, filed on Mar. 10, 1998, now Pat. No. 6,284,944.
(60) Provisional application No. 60/057,069, filed on Aug. 29, 1997.

(51) Int. Cl.$^7$ ................................................. C12N 5/00
(52) U.S. Cl. .............................. 800/3; 800/12; 800/18; 435/320.1
(58) Field of Search ........................... 800/3, 4, 12, 18; 435/320.1, 325, 455

(56) References Cited

U.S. PATENT DOCUMENTS

| | | | |
|---|---|---|---|
| 4,959,317 A | 9/1990 | Sauer ....................... 435/172.3 |
| 5,777,194 A | 7/1998 | Scott et al. ..................... 800/2 |
| 5,850,003 A | * 12/1998 | McLonlogue et al. | |
| 5,877,399 A | * 3/1999 | Hsiao et al. | |
| 5,898,094 A | 4/1999 | Duff et al. ..................... 800/2 |
| 5,986,054 A | 11/1999 | St. George-Hyslop et al. .. 530/350 |

FOREIGN PATENT DOCUMENTS

| | | |
|---|---|---|
| WO | WO 96/34097 | 10/1996 |
| WO | WO99/34670 | 7/1999 |

OTHER PUBLICATIONS

Rulicke et al. Special review series–gene manipulation and integrative physiology pp. 590–601 1996.*
Bishop Chromosomal insertion of foreign DNA pp. 607619 1996.*
Polejaeva et al. New advances in somatic cell nuclear transfer: application in transgenesis pp. 117–126 2000.*
Loring, Neurobiology of Aging, vol. 17, No. 2, pp. 173–182, 1996.*
Ganten (Biomedical and Health Res., 23 (human genome Analysis), 450–457, 1998).*
Ardis (abstract view, Society for Neuroscience Abstracts, 2001, vol. 27, No. 2, pp. 2344).*

Flood, D.G., et al, "FAD mutant PS–1 gene–targeted mice: Increased Aβ42 and Aβ deposition without APP overproduction," *Neurobiology of Aging*, 2002, 23, 335–348.
Savage, M. J., et al, "Presenilin–1 P264L, Knock–in Mutation: Effect on Cortical Neuronal Vulnerability to Degneration," *Dept. Pharmacology, Univ. Penna. School of Medicine, et al*, P.D. Oct. 23, 1999, XP–001089602, 1 page (Abstract).
Askew et al., "Site–Directed Point Mutations in Embryonic Stem Cells: a Gene–Targeting Tag–and–Exchange Strategy," *Mol. Cell Biol.*, 1993, 13(7), 4115–4124.
Borchelt et al., "Familial Alzheimer's Disease–Linked Presenilin 1 Variants Elevate Aβ1–42/1–40 Ratio In Vitro and In Vivo", *Neuron*, 1996, 17, 1005–1013.
Capecchi, M.R., "The New Mouse Genetics: Altering the Genome by Gene Targeting," *Trends Genet.*, 1989, 5(3), 70–76.
Cataldo et al., "Gene Expression and Cellular Content of Cathepsin D in Alzheimer's Disease Brain: Evidence for Early Up–Regulation of the Endosomal–Lysosomal System," *Neuron*, 1995, 14, 671–680.
Church et al., "Genomic sequencing," *Proc. Natl. Acad. Sci.*, 1984, 81, 1991–1995.
Clark et al., "The structure of the presenilin 1 (S182) gnee and identification of six novel mutations in early onset AD families," *Nature Genet.*, 1995, 11, 219–222.
Doan et al., "Protein Topology of Presenilin 1," *Neuron*, 1996, 17, 1023–1030.
Dower et al., "High efficiency transformation of *E. coli* by high voltage electroporation," *Nucl. Acids Res.*, 1988, 16(13), 6127–6145.
Duff et al., "Increased amyloid–β42(43) in brains of mice expressing mutant presenilin 1," *Nature*, 1996, 383, 710–713.
Fiering et al., "An "in–out" strategy using gene targeting and FLP recombinase for the functional dissection of complex DNA regulatory elements: Analysis of the β–globin locus control region," *Proc. Natl. Acad. Sci. USA*, 1993, 90, 8469–8473.
Gu et al., "Delection of a DNA Polymerase β Gene Segment in T Cells Using Cell Type–Specific Gene Targeting," *Science*, 1994, 265, 103–106.

(List continued on next page.)

*Primary Examiner*—Dave T. Nguyen
(74) *Attorney, Agent, or Firm*—Woodcock Washburn LLP

(57) ABSTRACT

The present invention provides a gene-targeted, non-human mammal having a gene encoding a mutant protein product of a mutated FAD presenilin-1 (PS-1) gene, a human FAD Swedish mutation, and a humanized Aβ mutation, and generational offspring thereof and a gene-targeted, non-human mammal having a gene encoding a mutant protein product of a mutated FAD PS-1 gene and a human Swedish APP695 mutation, and generational offspring thereof, as well as methods of identifying compounds useful in treating Alzheimer's disease, and to methods of treating Alzheimer's disease.

40 Claims, 19 Drawing Sheets

OTHER PUBLICATIONS

Gu et al., "Independent Control of Immunoglobulin Switch Recombination at Individual Switch Regions Evidenced through Cre–loxP Mediated Gene Targeting," *Cell,* 1993, 73, 1155–1164.

Haass, "Presenilins: Genes for Life and Death," *Neuron,* 197, 18, 687–690.

Holmes et al., "A Rapid Boiling Method for the Preparation of Bacterial Plasmids," *Anal. Biochem.,* 1981, 114, 193–197.

Kim et al., "Endoproteolytic Cleavage and Proteasomal Degradation of Presenilin 2 in Transfected Cells," *J. Biol. Chem.,* 1997, 272(17), 11006–11010.

Koller et al., "Altering Genes in Animals by Gene Targeting," *Ann. Rec. Immunol.,* 1992, 10, 705–730.

Kovacs et al., "Alzheimer–associated presenilins 1 and 2: Neuronal expression in brain and localization to intracellular membranes in mammalian cells," *Nature Med.,* 1996, 2(2), 224–229.

Lee et al., "Hyperaccumulation of FAD–linked presenilin 1 variants in vivo," *Nature Med.,* 1997, 3(7), 756–760.

Levitan et al., "Assessment of normal and mutant human presenilin function in *Caenorhabditis elegans,*" *Proc. Natl. Acad. Sci. USA,* 1996, 93, 14940–19444.

Levitan et al., "Facilitation of lin–12–mediated signalling by sel–12, a *Caenorhabditis elegans S182* Alzheimer's disease gene," *Nature,* 1995, 377, 351–354.

Levy–Lahad et al., "Candidate Gene for the Chromosome 1 Familial Alzheimer's Disease Locus," *Science,* 1995, 269, 973–977.

Mullis et al., "[21] Specific Synthesis of DNA in vitro via a Polymerase–Catalyzed Chain Reaction," *Methods Enzymol.,* 1987, 155, 335–350.

Nagy et al., "Derivation of completely cell culture–derived mice from early–passage embryonic stem cells," *Proc. Natl. Acad. Sci.,* 1993, 90, 8424–8428.

Reaume et al., "Cardiac Malformation in Neonatal Mice Lacking, Connexin43," *Science,* 1995, 267, 1831–1834.

Roganev et al., "Familial Alzheimer's disease in kindreds with missense mutations in a gene on chromosome 1 related to the Alzheimer's disease type 3 gene," *Nature,* 1995, 376, 775–778.

Rubinstein et al., "Introduction of a point mutation into the mouse genome by homologous recombination in embryonic stem cells using a replacement type vector with a selectable marker," *Nucl. Acid Res.,* 1993, 21(11), 2613–2617.

Salehi et al., "Decreased Activity of Hippocampal Neurons in Alzheimer's Disease Is Not Related to the Presence of Neurofibrillary Tangles," *J. Neuropath. Exp. Neurol.,* 1995, 54(5), 704–709.

Sanger et al., "DNA sequencing with chain–terminating inhibitors," *Proc. Natl. Acad. Sci.,* 1977, 74(12), 5463–5467.

Scheuner et al., "Secreted amyloid β–protein similar to that in the senile plaques of Alzheimer's disease is increased in vivo by the presenilin 1 and 2 and APP mutations linked to familial Alzheimer's disease," *Nature Med.,* 1996, 2(8), 864–870.

Sherrington et al., "Cloning of a gene bearing missense mutations in early–onset familial Alzheimer's disease," *Nature,* 1995, 375, 754–760.

Siman et al., "Strategies to alter the progression of Alzheimer's disease," *Curr. Opin. Biotech.,* 1996, 7, 601–607.

Slunt et al., "Nucleotide sequence of the chromosome 14–encoded S182 cDNA and revised secondary structure prediction," *Amyloid—Int. J. Exp. Clin. Invest.,* 1995, 2, 188–190.

te Riele et al., "Highly efficient gene targeting in embryonic stem cells through homologous recombination with isogenic DNA constructs," *Proc. Natl. Acad. Sci. USA,* 1992, 89, 5128–5132.

Thinakaran et al., "Endoproteolysis of Presenilin 1 and Accumulation of Processed Derivatives in Vivo," *Neuron,* 1996, 17, 181–190.

Tybulewicz et al., "Neonatal Lethality and Lymphopenia in Mice with a Homozygous Disruption of the c–abl Proto–Oncogene," *Cell,* 1991, 65, 1153–1163.

Wang et al., "Glycosylation of microtubule–associated protein tau: An abnormal posttranslational modification in Alzheimer's disease," *Nature Med.,* 1996, 2(8), 871–875.

Wasco et al., "Familial Alzheimer's chromosome 14 mutations," *Nature Med.,* 1995, 1(9), 848.

Wong et al., "Presenilin 1 is required for Notch1 and DII1 expression in the paraxial mesoderm," *Nature,* 1997, 387, 288–292.

Wood et al., "Non–injection methods for the production of embryonic stem cell–embryo chimaeras," *Nature,* 1993, 365, 87–89.

Wurst et al., "Production of targeted embryonic stem cell clones," in *Gene Targeting: A Practical Approach,* Joyner, A.L. (ed.), IRL Press, Oxford University Press, Oxford, England, 1993, Ch. 2, 33–61.

Hogan et al., in *Manipulating the Mouse Embryo: A Laboratory Manual,* Cold Spring Harbor Laboratory, Cold Spring Harbor, New York, 1986.

Maniatis et al., *Molecular Cloning—A Laboratory Manual,* 2nd edition, Cold Spring Harbor Press, 1989.

Ebert, K.M., "A moloney MLV–rat somatotropin fusion gene produces biologically active somatotropin in a transgenic pig," *Molecular Endocrinology,* 1988, 2, 277–283.

Hammer, R.E., et al., "Genetic engineering of mamalian embryos," *J. Animal Science,* 1986, 63, 269–278.

Koike, K., et al., "Expression of hepatitis C virus envelope proteins in transgenic mice," *J. Gen. Virology,* 1995, 76, 3031–3038.

Lee, M.K., et al., "Expression and endoproteolytic processing of wild type and FAD–linked mutant presenilin in transgenic mice," *Molecular Biology of the Cell 7 (Supplement),* 1996, 653A.

Palmiter, et al., *Ann. Rev. Genet,* 1986, 20, 465–499.

Palmiter, et al., *PNAS,* 1991, 88, 478–482.

Wasco, W., et al., "Familal alzheimer's chromosome 14 mutations," *Nat. Med.,* 1995, 1(9), 848.

Wall, *Theriogenology,* 1996, 43, 57–68.

Whitelaw, et al., *Transgenic Res.,* 1991, 1, 3–13.

Aldudo, J., et al., "DGGE method for the mutational analysis of the coding and proximal promoter regions of the alzheimer's disease presenilin–1 gene: two novel mutations," *Human Mutat.,* 1999, 14, 433–439.

Aldudo, J., et al., "Identification of a novel mutation (Leu282Arg) of the human presenilin 1 gene in alzheimer's disease," *Neurosci. Lett.,* 1998, 240, 174–176.

Besancon, R., et al., "Missense mutation in exon 11 (Codon 378) of the presenilin–1 gene in a French family with ear,ly–onset alzheimer's disease and transmission study by mismatch enhanced allele specific amplification," *Human Mutat.,* 1998, 11, 481 (abstract only).

Borchelt, D.R., et al., "Accelerated amyloid deposition in the brains of transgenic mice coexpressing mutant presenilin 1 and amyloid precursor proteins," *Neuron,* 1997, 19, 939–945.

Campion, D., et al., "Early–onset autosomal dominant alzheimer disease: prevalence, genetic heterogeneity, and mutation spectrum," *Am. J. Human Genet.,* 1999, 65, 664–670.

Campion, D., et al., "Mutations of the presenilin 1 gene in families with early–onset alzheimer's disease," *Hum. Molec. Genet.,* 1995, 4(12), 2373–2377.

Chui, D., et al., "Transgenic mice with alzheimer presenilin 1 mutations show accelerated neurodegeneration without amyloid plaque formation," *Nature Med.,* 1999, 5(5), 560–564.

Citron, M., et al., "Mutant presenilins of alzheimer's disease increase production of 42–residue amyloid β–protein in both transfected cells and transgenic mice," *Nature Med.,* 1997, 3(1), 67–72.

Cruts, M., et al., "Presenilin mutations in alzheimer's disease," *Human Mutat.,* 1998, 11, 183–190.

De Strooper, B., et al., "Phosphorylation, subcellular localization, and membrane orientation of the alzheimer's disease–associated presenilins," *J. Biol. Chem.,* 1997, 272(6), 3590–3598.

De Strooper, B., et al., "Deficiency of presenilin–1 inhibits the normal cleavage of amyloid precursor protein," *Nature,* 1998, 391, 387–390.

DeJonghe, C., et al., "Aberrant splicing in the presenilin–1 intron 4 mutation causes presenile alzheimer's disease by increased Aβ42 secretion," *Hum. Molec. Genet.,* 1999, 8(8), 1529–1540.

Dumanchin, C., et al., "De novo presenilin 1 mutations are rare in clinically sporadic, early onset alzheimer's disease cases," *J. Med. Genet.,* 1998, 35, 672–673.

Ezquerra, M., et al., "A presenilin 1 mutation (Ser169Pro) associated with early–onset AD and myoclonic seizures," *Neurol.,* 1999, 52, 566–570.

Ezquerra, M., et al., "A novel presenilin 1 mutation (Leu166Arg) associated with early–onset alzheimer disease," *Arch. Neurol.,* 2000, 57, 485–488.

Gómez–Isla, T., et al., "A novel presenilin–1 mutation: increased β–amyloid and neurofibrillary changes," *Annals of Neurol.,* 1997, 41(6), 809–813.

Guo, Q., et al., "Increased vulnerability of hippocampal neurons to excitotoxic necrosis in presenilin–1 mutant knock–in–mice," *Nature Med.,* 1999, 5(1), 101–106.

Hardy, J., "Amyloid, the presenilins and alzheimer's disease," *Trends Neurosci.,* 1997, 20(4), 154–159.

Hendriks, L., et al., "Processing of presenilin 1 in brains of patients with alzheimer's disease and controls," *NeuroReport,* 1997, 8(7), 1717–1721.

Hogan, et al., *Manipulating the Mouse Embryo: A Laboratory Manual,* 1986, Cold Spring Harbor Laboratory, Cold spring harbor, NY.

Holcomb, L., et al., "Accelerated alzheimer–type phenotype in transgenic mice carrying both mutant *amyloid* precursor protein and *presnilin 1* transgenes," *Nature Med.,* 1998, 4(1), 97–100.

Hsiao, K., et al., "Correlative memory deficits, Aβ elevation, and amyloid plaques in transgenic mice," *Science,* 1996, 274, 99–102.

Kamimura, K., et al., Familial alzheimer's disease genes in Japanese, *J. Neurol. Sci.,* 1998, 160, 76–81.

Kowalska, A., et al., "A Polish pedigree with alzheimer's disease determined by a novel mutation in exon 12 of the presenilin 1 gene: clinical and molecular characterization," *Folia Neuropath.,* 1999, 37(1), 57–61.

Lamb, B.T., et al., "Amyloid production and deposition in mutant *amyloid* precursor protein and *presenilin–1* yeast artificial chromosome transgenic mice," *Nature Neurosci.,* 1999, 2(8), 695–697.

Lemere, C., et al., "The E280A presenilin 1 alzheimer mutation produces increased Aβ42 deposition and severe cerebellar pathology," *Nature Med.,* 1996, 2(10), 1146–1150.

Lévesque, L., et al., "Developmental expression of wild–type and mutant presenilin–1 in hippocampal neurons from transgenic mice: evidence for novel species–specific properties of human presenilin–1," *Molec. Med.,* 1999, 5, 542–554.

Levey, A.I., et al., "Presenilin–1 protein expression in familial and sporadic alzheimer's disease," *Annals of Neurol.,* 1997, 41(6), 742–753.

Maniatis, et al., *Molecular Cloning—A Laboratory Manual, $2^{nd}$ ed.,* Cold Spring Harbor Press, 1989.

Mann, D.M.A., et al., "Amyloid β protein (Aβ) deposition in chromosome 14–linked alzheimer's disease: predominance of $A\beta_{42(43)}$," *Annals of Neurol.,* 1996, 40(2), 149–156.

Mercken, M., et al., "Characterization of human presenilin 1 using N–terminal specific monoclonal antibodies: evidence that alzheimer mutations affect proteolytic processing," *FEBS Lett.,* 1996, 389, 297–303.

Murayama, O., et al., "Different effects of alzheimer–associated mutations of presenilin–1 on its processing," *Neurosci. Lett.,* 1997, 229, 61–64.

Murayama, O., et al., "Enhancement of amyloid β 42 secretion by 28 different presenilin 1 mutations of familial alzheimer's disease," *Neurosci. Lett.,* 1999, 265, 61–63.

Murayama, O./, et al., "Twenty–nine missense mutations linked with familial alzheimer's disease alter the processing of presenilin 1," *Neuro–Psychopharmacol. Biol. Psychiatr.,* 1999, 23, 905–913.

Nakano, Y., et al., "Accumulation of murine amyloidβ42, in a gene–dosage–dependent manner in PS1 'knock–in' mice," *Europ. J. Neuroscience,* 1999, 11, 2577–2581.

Perez–Tur, J., et al., "A mutation in alzheimer's disease destroying a splice acceptor site in the presenilin–1 gene," *NeurReport,* 1995, 7, 297–301.

Podlisny, M.B., et al., "Presenilin proteins undergo heterogeneous endoproteolysis between $thr_{291}$ and $ala_{299}$ and occur a stable—and C–terminal fragments in normal and alzheimer brain tissue," *Neurobiol. Dis.,* 1997, 3, 325–337.

Prihar, G., et al., "Alzheimer disease PS–1 exon 9 deletion defined," *Nature Med.,* 1999, 5(10), 1090.

Qian, S., et al., "Mutant human presenilin 1 protects presenilin 1 nul mouse against embryonic lethality and elevates Aβ1–42/43 expression," *Neuron,* 1998, 20, 611–617.

Reaume, A.G., et al., "Enhanced amyloidogenic processing of the β–amyloid precursor protein in gene–targeted mice bearing the swedish familial alzheimer's disease mutations and a "humanized" Aβsequence," *J. Biol. Chem.,* 1996, 271(38), 23380–23388.

Romero, I., et al., "A presenilin–1 thr116asn substitution in a family with early–onset alzheimer's disease," *NeuroReport,* 1999, 10(11), 2255–2260.

Sato, S., et al., "Splicing mutation of presenilin–1 gene for early–onset familial alzheimer's disease," *Hum. Mutat. Suppl.,* 1998, 1, S91–94.

Sauer, B., et al., "Targeted insertion of exogenous DNA into the eukaryotic genome by the cre recombinase," *New Biol.,* 1990, 2(5), 441–449.

Savage, M.J., et al., "Cathespin G: localization in human cerebral cortex and generation of amyloidogenic fragments from the β–amyloid precursor protein," *Neurosci.,* 1994, 60(3), 607–619.

Savage, M.J., et al., "Turnover of amyloid β–protein in mouse brain and acute reduction of its level by phorbol ester," *J. Neurosci.,* 1998, 18(5), 1743–1752.

Shen, J., et al., "Skeletal and CNS defects in presenilin–1–deficient mice," *Cell,* 1997, 89, 629–639.

Smith, M.J., et al., "Early–onset alzheimer's disease caused by a novel mutation at codon 219 of the presenilin–1 gene," *NeuroReport,* 1999, 10, 503–507.

St. George–Hyslop, P.H., "Molecular genetics of alzheimer's disease," *Biol. Psychiatr.,* 2000, 47, 183–199.

Sugiyama, N., et al., "A novel missense mutation (G209R) in exon 8 of the presenilin 1 gene in a Japanese family with presenile familial alzheimer's disease," *Online Human Mutat.,* 1999, 14, 90.

Taddei, K., et al., "Two novel presenilin–1 mutations (Ser169Leu and Pro436Gln) associated with very early onset alzheimer's disease," *NeuroReport,* 1998, 9(14), 3335–3339.

Takahashi, H., et al., "Impaired proteolytic processing of presenilin–1 in chromosome 14–linked familial alzheimer's disease patient lymphocytes," *Neurosci. Lett.,* 1999, 260, 121–124.

Theuns, J., et al., "Genetic variability in the regulatory region of presnilin 1 associated with risk for alzheimer's disease and variable expression," *Human Molec. Genet.,* 2000, 9(3), 325–331.

Vanderhoeven, I., et al., "proteolytic processing of presenilin–1 in human lymphoblasts is not affectedby the presence of the 1143T and G384A mutations," *Neurosci. Lett.,* 1999, 274, 183–186.

Weibel, E.R. (ed.), "Practical methods for biological morphometry," *Stereological Methods,* 1979, 1, Academic Press, London.

Yasuda, M., et al., "Novel presenilin–1 mutation with widespread cortical amyloid deposition but limited cerebral amyloid angiopathy," *J. Neural. Neurosurg. Psychiatr.,* 2000, 68, 220–223.

Yasuda, M., et al., "A pedigree with a novel presenilin 1 mutation at a residue that is not conserved in presenilin 2," *ARCH Neurol,* 1999, 56, 65–69.

Yasuda, M., et al., "A novel missense mutation in the presenilin–1 gene in a familial alzheimer's disease pedigree with abundant amyloid angiopathy," *Neuroscience Letts.,* 1997, 232, 29–32.

\* cited by examiner pPS1-X319 Construction

Example of Restriction Mapping the 5' Arm of Homology

GENE-TARGETED NON-HUMAN MAMMAL WITH HUMAN FAD PRESENILIN MUTATION AND GENERATIONAL OFFSPRING

CROSS REFERENCE TO RELATED APPLICATIONS

The present application is a continuation-in-part and claims priority under 35 U.S.C. §120 to U.S. Ser. No. 09/041,185 now U.S. Pat. No. 6,284,944 filed Mar. 10, 1998, which claims priority under 35 U.S.C. §119(e) to Provisional Serial No. 60/057,069 filed Aug. 29, 1997, each of which are incorporated herein by reference in its entirety.

FIELD OF THE INVENTION

The present invention relates to gene-targeted, non-human mammals comprising a human mutation in the non-human mammalian presenilin 1 (PS-1) FAD gene, methods of identifying compounds for treating Alzheimer's disease, and to methods of treating Alzheimer's disease.

BACKGROUND OF THE INVENTION

Alzheimer's disease (AD) is an age-dependent neurodegenerative disorder that leads to profound behavioral changes and dementia. Hallmark pathologies include the atrophy of brain gray matter as a result of the massive loss of neurons and synapses, and protein deposition in the form of both intraneuronal neurofibrillary tangles and extracellular amyloid plaques within the brain parenchyma. In addition, affected areas of the AD brain exhibit a reactive gliosis that appears to be a response to brain injury. Surviving neurons from vulnerable populations in AD show signs of metabolic compromise as indicated by alterations in the cytoskeleton (Wang et al., *Nature Med.*, 1996, 2, 871–875), Golgi complex (Salehi et al., *J. Neuropath. Exp. Neurol.*, 1995, 54, 704–709) and the endosomal-lysosomal system (Cataldo et al., *Neuron*, 1995, 14, 671–680).

Approximately 10 to 30% of AD cases are inherited in an autosomal dominant fashion and are referred to as "familial Alzheimer's disease" or "FAD." Genetic linkage studies have revealed that FAD is heterogeneous and a majority of the cases have been linked to gene mutations on chromosomes 1, 14, 19, or 21 (reviewed in Siman and Scott, *Curr. Opin. Biotech.*, 1996, 7, 601–607). Importantly, these individuals have been shown to develop the classical symptomatic and pathological profiles of the disease confirming that the mutations are associated with the development of the disease rather than a related syndrome. The locus on chromosome 14 is associated with a significant fraction of FAD, and mutations at the locus have been mapped to a single-copy gene, termed "S182" or "presenilin 1" (PS-1), that encodes a 467 amino acid protein (Sherrington et al., *Nature*, 1995, 375, 754–760; Clark et al., *Nature Genet.*, 1995, 11, 219–222). A closely related gene, "STM2" or "presenilin 2" (PS-2), located on chromosome 1, has been linked to two additional FAD kindreds including the descendants of German families from the Volga valley of Russia (Levy-Lahad et al., *Science*, 1995, 269, 973–977; Rogaev et al., *Nature*, 1995, 376, 775–778). PS-1 and PS-2 share an overall 67% amino acid sequence homology, and primary structure analysis indicates they are integral membrane proteins with 6 to 8 trans-membrane domains (Slunt et al., *Amyloid—Int. J Exp. Clin. Invest.*, 1995, 2, 188–190; Doan et al., *Neuron*, 1996, 17, 1023–1030). Much of the information on function of the presenilins stems from the identification of a presenilin homolog in *C. elegans* termed "SEL-12," a 6 to 8 trans-membrane protein that appears to participate in an intracellular signaling pathway mediated by the lin-12/glp-1/Notch family (Levitan and Greenwald, *Nature*, 1995, 377, 351–354). PS-1 and SEL-12 proteins share a 49% sequence homology and have similar membrane orientations. Importantly, both human PS-1 and PS-2 can rescue the mutant sel-12 phenotype in *C. elegans*, indicating a role for the presenilins in Notch signaling (Levitan et al., *Proc. Natl. Acad. Sci. USA*, 1996, 93, 14940–14944).

FAD linked to the presenilins is highly penetrant and the aggressive nature of the disease suggests that the mutant protein participates in a seminal pathway of AD pathology. To date, over seventy FAD mutations have been identified in PS-1, and three FAD mutations have been found in PS-2. Most of the FAD mutations occur in conserved positions between the two presenilin proteins, suggesting that they are affecting functionally or structurally important amino acid residues. Interestingly, many of the mutated amino acids are also conserved in SEL-12. All but two of the presenilin mutations are missense mutations. One exception results in an aberrant RNA splicing event that climninates exon 9, creating an internally-deleted mutant protein (Perez-Tur et al., *NeuroReport*, 1995, 7, 297–301; Sato et al., *Hum. Mutat. Suppl.*, 1998, 1, S91–94; and Prihar et al., *Nature Med.*, 1999, 5, 1090). The other results in two deletion transcripts (Δ4 and Δ4cryptic) and one full-length transcript with the amino acid Thr inserted between 113 and 114 (DeJonghe et al., *Hum. Molec. Genet.*, 1999, 8, 1529–1540). The latter transcript leads to the AD pathophysiology. These latter points, along with the genetic dominance of the disease, argue that disease pathogenesis in the presenilin kindreds requires the production of a mutant presenilin protein having a novel and detrimental function, rather than the simple loss or reduction of normal presenilin levels. The mutations do appear to disrupt normal presenilin function however, because mutant presenilins are not able to rescue or fully rescue the sel-12 phenotype (Levitan et al., *Proc. Natl. Acad. Sci. USA*, 1996, 93, 14940–14944).

Expression profiles of the presenilins have been examined at a gross level but, so far, these analyses have yielded little information on the mechanism of disease pathogenesis. Both presenilin 1 and 2 are widely expressed in the CNS and peripheral tissues. In brain, expression is enriched in neurons but is apparent in both AD-vulnerable and resistant areas. Cellular localization studies indicate that the proteins accumulate primarily in the Golgi complex and endoplasmic reticulum but no significant alterations in expression levels or subcellular distribution have been attributed to the FAD mutations (Kovacs et al., *Nature Med.*, 1996, 2, 224–229).

The presenilin proteins are processed proteolytically through two intracellular pathways. Under normal conditions, accumulation of 30 kD N-terminal and 20 kD C-terminal proteolytic fragments occurs in the absence of the full-length protein. This processing pathway is highly regulated and appears to be relatively slow, accounting for turnover of only a minor fraction of the full-length protein. The remaining fraction appears to be rapidly degraded in a second pathway by the proteasome (Thinakaran et al., *Neuron*, 1996, 17, 181–190; Kim et al., *J. Biol. Chem.*, 1997, 272, 11006–11010). Proteolytic metabolism of PS-1 variants linked to FAD appears to be different, but the relevance of the change to pathogenesis is not known (Lee, et al., *Nature Med.*, 1997, 3, 756–760).

One pathogenic role for the mutant presenilins in FAD appears to be related to effects on processing of the amnyloid precursor protein (APP) and production of the Aβ peptide, the primary proteinaceous component of the extracellular neuritic plaque in the AD brain. Elevated serum levels of the longer form of Aβ (Aβ42), considered to be the more pathogenic species of the Aβ peptides, have been measured in patients bearing PS-1 and PS-2 mutations (Scheuner et al., *Nature Med.*, 1996, 2, 864–870). Additionally, FAD brains with PS-1 mutations have large amounts of Aβ deposition (Lemere et al., *Nature Med.*, 1996, 2, 1146–1150; Mann et al., *Ann. Neurol.*, 1996, 40, 149–156; Gómez-Isla et al., *Ann. Neurol.*, 1997, 41, 809–813). Elevated levels of Aβ1-42 were also found in cells transfected with mutant PS-1 or PS-2 and in mice expressing mutant PS-1 (Borchelt et al., *Neuron*, 1996, 17, 1005–1013; Duff et al., *Nature*, 1996, 383, 710–713; Citron et al., *Nature Med.*, 1997, 3, 67–72; Murayama et al., *Prog. Neuro-Psychopharmacol. Biol. Psychiatr.*, 1999, 23, 905–913; Murayama et al., *Neurosci. Lett.*, 1999, 265, 61–63; Nakano et al., *Eur. J. Neurosci.*, 1999, 11, 2577–2581). The mechanism by which the mutant presenilins affect APP processing is not known, but these results do support a causative role of increased Aβ42 production in the development of FAD. Importantly, it is possible that mutant presenilins influence other AD pathogenic processes as well, such as presumptive intracellular signaling and cell death pathways involved directly or indirectly in neuronal dysfunction and degeneration.

Genetically-engineered animals have been used extensively to examine the function of specific gene products in vivo and their role in the development of disease phenotypes. The genetic engineering of mice can be accomplished according to at least two distinct approaches: (1) a transgenic approach where an exogenous gene is randomly inserted into the host genome, and (2) a gene-targeting approach where a specific endogenous DNA sequence or gene is partially or completely removed, or replaced by homologous recombination. The transgene of a transgenic organism is comprised generally of a DNA sequence encoding the protein sequence and a promoter that directs expression of the protein coding sequences. A transgenic organism expresses the transgene in addition to all normally-expressed native genes. The targeted gene of a gene-targeted animal, on the other hand, can be modified in one of two ways: (1) a functional form where a modified version of the targeted gene is expressed, or (2) a non-functional or "null" form where the targeted gene has been disrupted resulting in loss or reduction of expression. If the targeted gene is a single copy gene and the animal is homozygous at the targeted locus, then, depending on the type of modification, the animal either does not express the targeted gene or expresses only a modified version of the targeted gene in absence of the normal form.

Transgenic mice expressing native and mutant forms of the presenilin proteins have been described (Borchelt et al., *Neuron*, 1996, 17, 1005–1013; Duff et al., *Nature*, 1996, 383, 710–713; Borchelt et al., *Neuron*, 1997, 19, 939–945; Citron et al., *Nature Med.*, 1997, 3, 67–72; Chui et al., *Nature Med.*, 1999, 5, 560–564; and Nakano et al., *Eur. J. Neurosci.*, 1999, 11, 2577–2581). Although mice bearing mutations in PS-1 had elevated levels of Aβ1-42, they have not formed Aβ deposits characteristic of AD or shown behavioral deficits associated with AD. Neuronal loss has been described by one group (Chui et al., *Nature Med.*, 1999, 5, 560–564). When transgenic mice with PS-1 mutations were crossed with transgenic mice bearing the Swedish APP mutations, there was marked acceleration in the formation of Aβ deposits (Borchelt et al., *Neuron*, 1997, 19, 939–945; Holcomb et al., *Nature Med.*, 1998, 4, 97–100; Lamb et al., *Nature Neurosci.*, 1999, 2, 695–697). Gene-targeted PS-1 null mice lacking one or both functional alleles of the PS-1 gene have also been described (Wong et al., *Nature*, 1997, 387, 288–292, and Shen et al., *Cell*, 1997, 89, 629–639). Mice in which both PS-1 alleles have been disrupted resulting in the complete loss of PS-1 expression are not viable and die shortly after birth. No abnormal phenotypes or changes in APP processing have been reported in mice lacking only one of the two PS-1 alleles, but inhibition of APP processing is found in neurons derived from PS-1 null mice (DeStrooper et al., *Nature*, 1998, 391, 387–390).

In the present application, a gene-targeting approach (Reaume et al., *J. Biol. Chem.*, 1996, 271, 23380–23388, which is incorporated herein by reference in its entirety) generating AD models is described. One model employs the Swedish FAD mutation and "humanized" mouse Aβ sequence in the APP gene (U.S. Pat. No. 5,777,194, which is incorporated herein by reference in its entirety). This mouse ($APP^{NLh/NLh}$) produced normal levels of APP, overproduced human Aβ1-40 and 1-42, but did not deposit Aβ (Reaume et al., *J. Biol. Chem.*, 1996, 271, 23380–23388). A human PS-1 mutation, the P264L mutation in particular, was introduced into the mouse PS-1 gene. The P264L mutation is a non-conservative amino acid substitution in the cluster of mutations in exon 8, causing an onset of FAD in the middle forties to middle fifties (Campion et al., *Hum. Molec. Genet.*, 1995, 4, 2373–2377; Wasco et al., *Nature Med.*, 1995, 1, 848). Crosses produced $APP^{NLh/NLh} \times PS-1^{P264L/P264L}$ double gene-targeted mice. These mice had elevated levels of Aβ1-42, sufficient to cause Aβ deposition. Mice bearing the $PS-1^{P264L}$ mutation were also crossed with Tg2576 mice that overexpress Swedish APP695 (Hsiao et al., *Science*, 1996, 274, 99–102; available from the Mayo Clinic, Rochester, Minn.). One distinct advantage of the present invention is that for heterozygous and homozygous gene-targeted mice, the fidelity of expression patterns of proteins is maintained since the expression is under the endogenous promoter. Further, expression levels of the holoprotein are not changed.

SUMMARY OF THE INVENTION

The present invention relates to a gene-targeted, non-human mammal comprising a gene encoding a mutant protein product of a mutated FAD presenilin-1 (PS-1) gene, a human FAD Swedish mutation, and a humanized Aβ mutation, and generational offspring thereof. The present invention also relates to a gene-targeted, non-human mammal comprising a gene encoding a mutant protein product of a mutated FAD presenilin-1 (PS-1) gene and a human Swedish APP695 mutation, and generational offspring thereof Preferably, the PS-1 gene has been mutated to contain the human P264L mutation (Wasco et al., *Nature Medicine*, 1995, 1, 848). In particular, the present invention relates to a mouse wherein a part of a mouse presenilin 1 gene encoding presenilin 1 protein has been replaced with a DNA sequence that results in a mouse presenilin 1 gene that contains a human mutation, most preferably a P264L mutation. Still more specifically, the base sequence of codon 264 of the mouse presenilin 1 gene is altered from CCG to CTT, which is the base sequence found to constitute the P264L mutation of humans. The mutated gene codon encodes leucine in place of proline in amino acid number 264 of presenilin 1. Additionally, and still more specifically, a nucleotide base in codon 265 of the mouse presenilin 1 gene is altered from adenosine to guanosine, but this change does not result in an amino acid change in the expressed protein. However, the combined sequence of codons 264 and 265, after the incorporation of the most preferred changes described above, results in a restriction enzyme site for the restriction enzyme AflII.

Accordingly, in one embodiment, the present invention features a non-human mammal and generational offspring homozygous for a targeted mutant PS-1 gene comprising a mutated FAD gene preferably a mouse presenilin 1 protein-encoding sequence comprising a human mutation, most preferably a P264L mutation, in place of the native presenilin 1 protein-encoding sequence. In another embodiment, the invention features a non-human mammal and generational offspring heterozygous for a targeted PS-1 gene comprising a mutated mouse FAD gene, preferably a mouse presenilin 1 protein-encoding sequence containing a human mutation, most preferably a P264L mutation, in place of the native presenilin 1 protein-encoding sequence.

The present invention is also directed to methods for identifying a compound for treating Alzheimer's disease comprising administering a compound to a mammal heterozygous or homozygous for a mutation of the PS-1 gene and a human Swedish APP695 mutation, or generational offspring thereof, or to a mammal heterozygous or homozygous for a mutation of the PS-1 gene, a human FAD Swedish mutation, and a humanized Aβ mutation, and generational offspring thereof, and measuring the amount of Aβ42 peptide in a tissue sample from the mammal.

The present invention is also directed to methods of treating an individual suspected of having Alzheimer's disease comprising administering to the individual an effective Alzheimer's disease treatment amount of a compound identified by the method described above.

The present invention is also directed to compounds identified by any of the methods described above.

DESCRIPTION OF PREFERRED EMBODIMENTS

Figure 1:
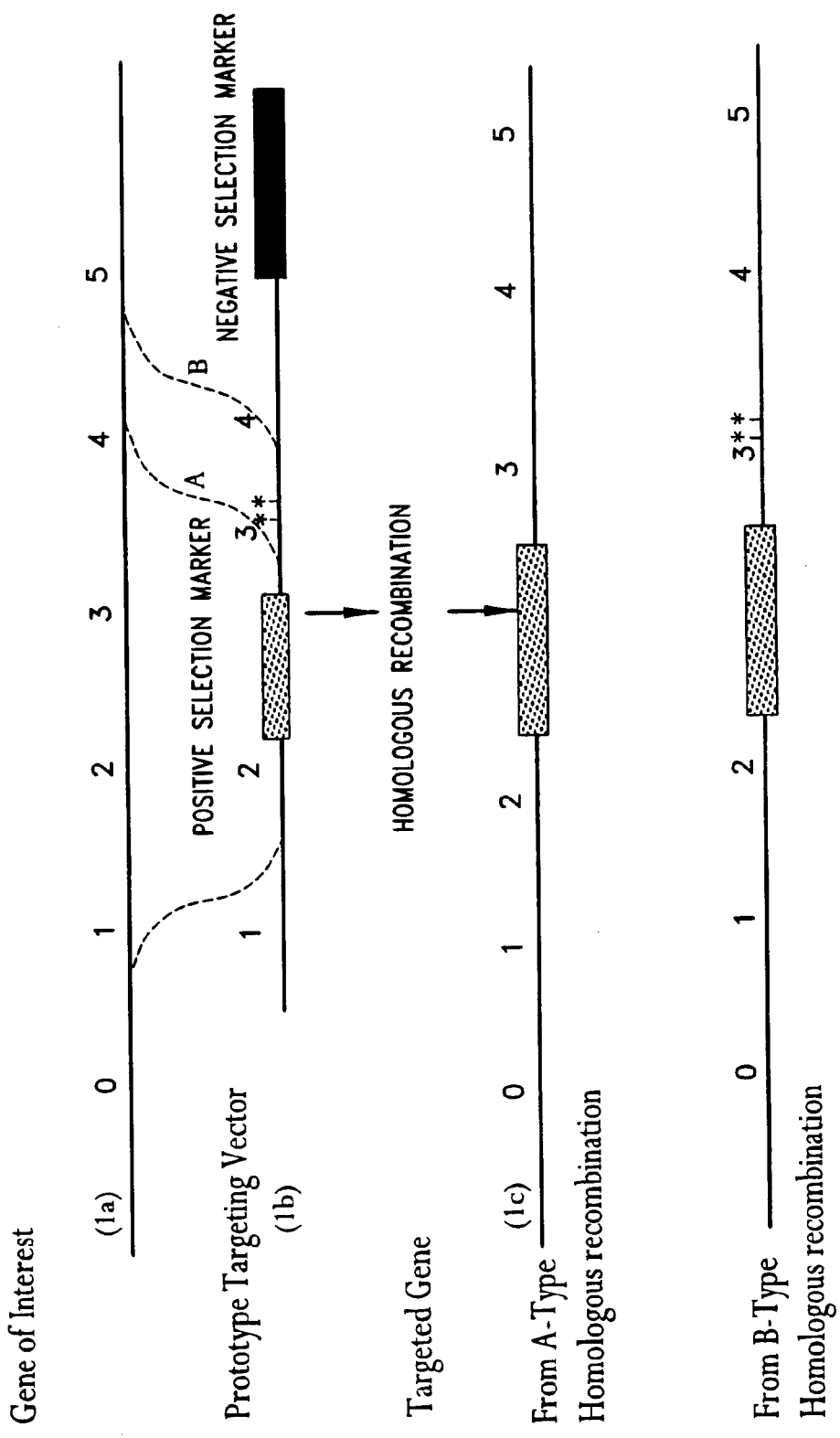
FIG. 1 is a schematic diagram illustrating general principles of gene targeting.

The present invention relates to a gene-targeted, non-human mammal (and generational offspring of such mammal) that contains in the non-human mammal's endogenous (i.e., native) genome presenilin 1 gene that comprises a human mutation, most preferably a human P264L mutation. The non-human mammal can also comprise a human FAD Swedish mutation and a humanized Aβ mutation. A non-human mammal can also comprise, in addition to the human PS-1 mutation, a human Swedish APP695 mutation. Most preferably, the gene-targeted, non-human mammal produces a mutated presenilin 1 protein instead of the presenilin 1 protein normally produced by the non-human mammal. Gene-targeted, non-human mammals homozygous for a presenilin 1 gene containing a human mutation, such as the human P264L mutation, produce the mutated presenilin 1 protein exclusively. Gene-targeted, non-human mammals heterozygous for a presenilin 1 gene containing a human mutation, such as the human P264L mutation, produce both the mutated presenilin 1 protein and the native presenilin 1 protein. Preferably, the gene-targeted, non-human mammal of this invention is a rodent, and more specifically a mouse.

Importantly, because the non-human mammal of this invention is generated by gene targeting, as opposed to transgenic techniques, the mammal produces the mutated presenilin 1 protein exclusively by normal endogenous presenilin 1 protein expression mechanisms. Advantageously, and unlike expression resulting from transgenic approaches, the presenilin 1 protein is expressed from genes having the normal copy number, and under the control of the endogenous presenilin 1 gene expression control mechanisms. As a result, the presenilin 1 protein in the non-human animal of this invention is produced with the same developmental timing, same tissue specificity, and same rates of synthesis normally associated with native presenilin 1 protein in the wild-type, non-human mammal.

The gene-targeted, non-human mammals of this invention may be used as tools or models to elucidate the role of PS-1 comprising a human mutation, preferably the human P264L mutation, in the pathology and symptomatology of AD. They may be used to elucidate the manner in which the human mutation, preferably the P264L mutation, increases the production of the amyloid protein Aβ42. As used herein, the term "increase" when used in the foregoing context, means that the levels of Aβ42 produced by the non-human mammals disclosed herein are elevated relative to wild-type controls.

The non-human mammals of this invention and generational offspring also may be used as assay systems to screen for in vivo inhibitors and for discovering and testing the efficacy and suitability of putative chemical compounds for their ability to inhibit the formation, presence and deposition of excessive amounts of Aβ peptide in the brain tissues, other tissues and body fluids (e.g., blood, plasma, and cerebrospinal fluid), said method comprising the steps of: (a) administering said chemical compounds to a non-human mammal homozygous or heterozygous for a targeted mutant PS-1 gene comprising a human mutation, preferably the human P264L mutation, comprising: a mouse PS-1 peptide encoding sequence containing a human mutation, preferably the P264L mutation, in place of the native PS-1 peptide encoding sequence and (b) measuring the amounts of Aβ peptide in brain tissues, other tissues and body fluids (or some combination thereof) of said non-human mammal, at an appropriate interval of time after the administration of said chemical compounds.

As used in this disclosure, the following terms and phrases have the following indicated definitions.

As used herein, "Aβ peptide" means either Aβ40 or Aβ42 or fragments thereof.

As used herein, "arms of homology" means nucleotide DNA sequences in a targeting vector: (1) which have sufficient length and homology to provide for site-specific integration of part of the targeting vector into the target gene by homologous recombination; (2) in which, or between which are located one or more mutations to be introduced into a target gene; and (3) which flank a positive selectable marker.

As used herein, "homologous recombination" means rearrangement of DNA segments, at a sequence-specific site (or sites), within or between DNA molecules, through base-pairing mechanisms.

As used herein, "human mutation in the non-human mammalian presenilin 1 (PS-1) FAD gene" means any mutation of the PS-1 gene in a non-human mammal that results in the non-human mammal having a nucleotide or nucleotides that correspond to the human PS-1 gene at the corresponding position of the nucleotide or nucleotides. A human mutation in the non-human mammalian presenilin 1 (PS-1) FAD gene includes, but is not limited to, the following: A79V, V82L, V96F, Y115C, E120D, E120K, M139I, M139T, M139V, I143F, I143T, M146I, M146L (A→T), H163Y, G209V, A231T, A231V, M233T, L235P, L250S, A260V, L262F, C263R, P264L, P267S, R269H, R278T, E280A, E280G, A285V, E318G, G378E, G384A, and L392V, each of which is disclosed in Cruts et al., *Human Mutat.*, 1998, 11, 183–190, which is incorporated herein by reference in its entirety; M146L (A→C) which is disclosed in Cruts et al., *Human Mutat.*, 1998, 11, 183–190, Duff et al., *Nature*, 1996, 383, 710–713, Citron et al., *Nature Med.*, 1997, 3, 67–72, Lee et al., *Nature Med.*, 1997, 3, 756–760, and Lamb et al., *Nature Neurosci.*, 1999, 2, 695–697, each of which is incorporated herein by reference in its entirety; M146V, which is disclosed in Cruts et al., *Human Mutat.*, 1998, 11, 183–190, Duff et al., *Nature*, 1996, 383,710–713, and Guo et al., *Nature Med.*, 1999, 5, 101–106, each of which is incorporated herein by reference in its entirety; H163R, which is disclosed in Cruts et al., *Human Mutat.*, 1998, 11, 183–190, Lamb et al., *Nature Neurosci.*, 1999, 2, 695–697, and Chui et al., *Nature Med.*, 1999, 5, 560–564, each of which is incorporated herein by reference in its entirety; I213T, which is disclosed in Cruts et al., *Human Mutat.*, 1998, 11, 183–190 and Nakano et al., *Eur. J. Neurosci.*, 1999, 11, 2577–2581, each of which is incorporated herein by reference in its entirety; L286V, which is disclosed in Cruts et al., *Human Mutat.*, 1998, 11, 183–190, Citron et al., *Nature Med.*, 1997, 3,67–72, and Chui et al., *Nature Med.*, 1999, 5, 560–564, each of which is incorporated herein by reference in its entirety; A246E, which is disclosed in Cruts et al., *Human Mutat.*, 1998, 11, 183–190, Lee et al., *Nature Med.*, 1997, 3, 756–760, and Qian et al., *Neuron*, 1998, 20, 611–617, each of which is incorporated herein by reference in its entirety; Y115H, which is disclosed in Citron et al., *Nature Med.*, 1997, 3, 67–72, which is incorporated herein by reference in its entirety; T116N, which is disclosed in Romero et al., *NeuroReport.*, 1999, 10, 2255–2260, which is incorporated herein by reference in its entirety; P117L and L171P, both of which are disclosed in St. George Hyslop, *Biol. Psychiatr.*, 2000, 47, 183–199, which is incorporated herein by reference in its entirety; E123L, which is disclosed in Yasuda et al., *Arch. Neuro.*, 1999, 56, 65–69, which is incorporated herein by reference in its entirety; N135D, C410Y, A426P and P436S, each of which is disclosed in Hardy et al., *Trends Neurosci.*, 1997, 20, 154–159, which is incorporated herein by reference in its entirety; M139K, which is disclosed in Dumanchin et al., *J. Med. Genet.*, 1998, 35, 672–673, which is incorporated herein by reference in its entirety; T147I, W165C, L173W, and S390I, each of which i s disclosed in Campion et al., *Am. J. Human Genet.*, 1999, 65, 664–670, which is incorporated herein by reference in its entirety; L166R, which is disclosed in Ezquerra et al., *Arch. Neurol.*, 2000, 57, 485–488, which is incorporated herein by reference in its entirety, S169L and P436Q, each of which is disclosed in Taddei et al., *Neuroreport.*, 1998, 9, 3335–3339, which is incorporated herein by reference in its entirety; S169P, which is disclosed in Ezquerra et al., *Neurol.*, 1999, 52, 566–570, which is incorporated herein by reference in its entirety; E184D, which is disclosed in Yasuda et al., *Neurosci. Lett.*, 1997, 232, 29–32, which is incorporated herein by reference in its entirety; G209R, which is disclosed in Sugiyama et al., *Online Human Mutat.*, 1999, 14, 90, which is incorporated herein by reference in its entirety; L219P, which is disclosed in Smith et al., *Neuroreport.*, 1999, 10, 503–507, which is incorporated herein by reference in its entirety; M233L and A409T, both of which are disclosed in Aldudo et al., *Human Mutat.*, 1999, 14, 433–439, which is incorporated herein by reference in its entirety; E273A, which is disclosed in Kamimura et al., *J. Neurol. Sci.*, 1998, 160, 76–81, which is incorporated herein by reference in its entirety; L282R, which is disclosed in Aldudo et al., *Neurosci. Lett.*, 1998, 240, 174–176, which is incorporated herein by reference in its entirety; G378A, which is disclosed in Besancon et al., *Human Mutat.*, 1998, 11, 481, which is incorporated herein by reference in its entirety; N405S, which is disclosed in Yasuda et al., *J. Neurol. Neurosurg. Psychiatr.*, 2000, 68, 220–223, which is incorporated herein by reference in its entirety; A409T, which is disclosed in Sugiyama et al., *Online Human Mutat.*, 1999, 14, 90, which is incorporated herein by reference in its entirety; L424R, which is disclosed in Kowalska et al., *Folia Neuropath.*, 1999, 37, 57–61, which is incorporated herein by reference in its entirety; a Delta exon 9 splice acceptor site deletion mutation (G→T with S290C), which is disclosed in Hardy et al., *Trends Neurosci.*, 1997, 20, 154–159 and Lee et al., *Nature Med.*, 1997, 3, 756–760, each of which is incorporated herein by reference in its entirety; a Delta exon 9 splice acceptor site deletion mutation (G→A with S290C), which is disclosed in Sato et al., *Human Mutat. Supp.*, 1998, 1, S91–94, which is incorporated herein by reference in its entirety; a Delta exon 9 Finn 4,555 basepair deletion, which is disclosed in Prihar et al., *Nature Med.*, 1999, 5, 1090, which is incorporated herein by reference in its entirety; a Delta intron 4 splice donor consensus sequence G deletion, which is disclosed in DeJonghe et al., *Human Molec. Genet.*, 1999, 8, 1529–1540, which is incorporated herein by reference in its entirety; and a C→T mutation at position-48 in the 5' promoter, a C→G mutation at position-280 in the 5' promoter, and an A→G mutation at position-2818 in the 5' promoter, each of which is disclosed in Theuns et al., *Human Molec. Genet.*, 2000, 9, 325–331, which is incorporated herein by reference in its entirety. Although the application exemplifies the P264L mutation in particular, all aspects of the invention can be applied to each and every human mutation recited above.

As used herein, "human P264L mutation" means the following: the nucleotide sequence of codon 264 of the presenilin 1 gene is changed from CCG to a sequence selected from the group consisting of: CTT; CTC; CTA; CTG; TTA; TTG; and most preferably changed from CCG to CTT. Additionally, the nucleotide sequence of codon 265 of the presenilin 1 gene optionally, but preferably, is changed from AAA to AAG. The above described most preferable change of base sequences in codon 264 constitute the human P264L mutation. The optional, but preferred, change of the base sequence of codon 265 adds an AflII cleavage site to the gene.

As used herein, "target gene" or "targeted gene" means a gene in a cell, which gene is to be modified by homologous recombination with a targeting vector.

As used herein, "gene-targeted, non-human mammal" means a non-human mammal comprising one or more targeted genes via a gene-targeting, as opposed to transgenic, approach.

As used herein, "generational offspring" in relationship to "gene-targeted, non-human mammal" means an animal whose genome includes the same gene-targeted manipulation as the parent(s) of that offspring. For example, and not limitation, where a mammal whose genome has been manipulated by gene-targeting techniques to include a human mutation is then used for breeding purposes, all subsequent generations derived from that first mammal(s) are considered "generational offspring" so long as the genome(s) of such subsequent generational offspring comprises the gene-targeted manipulation as the original mammal; by design, this definition does not exclude other genomic-manipulations which may also be present in such generational offspring, nor does this definition require that such generational offspring be derived solely by crossbreeding techniques between a male and female mammal.

As used herein, "transgenic non-human mammal" means a non-human mammal in which a foreign ("transgene") gene sequence has been inserted randomly in a non-human mammal's genome and is therefore expressed in addition to all normally expressed native genes (unless the inserted transgene has interrupted a gene thus preventing its expression).

As used herein, "targeting vector" or "replacement vector" means a DNA molecule that includes arms of homology, the nucleotide sequence (located within or between the arms of homology) to be incorporated into the target gene, and one or more selectable markers.

As used herein, "wild-type control animal" means a non-gene-targeted, non-human mammal of the same species as, and otherwise comparable to (e.g., similar age), a gene-targeted non-human mammal as disclosed herein. A wild-type control animal can be used as the basis for comparison, in assessing results associated with a particular genotype.

Other features and advantages of the invention will be apparent from the following description of the preferred embodiments thereof, and from the claims.

The first step in producing a gene-targeted non-human mammal of this invention is to prepare a DNA targeting vector. The targeting vector is designed to replace, via homologous recombination, part of the endogenous presenilin 1 gene sequence of a non-human mammal, so as to introduce the human mutation, preferably the P264L human mutation. The targeting vector is used to transfect a non-human mammalian cell, e.g., a pluripotent, murine embryo-derived stem ("ES") cell. In this cell, homologous recombination (i.e., the gene-targeting event) takes place between the targeting vector and the target gene. The mutant cell is then used to produce intact non-human mammals (e.g., by aggregation of murine ES cells to mouse embryos) to generate germ-line chimeras. The germline chimeras are used to produce siblings heterozygous for the mutated targeted gene. Finally, interbreeding of heterozygous siblings yields non-human mammals (e.g., mice) homozygous for the mutated target gene.

Targeting vectors for the practice of this invention can be constructed using materials, information and processes known in the art. A general description of the targeting vector used in this invention follows.

A targeting vector or replacement vector for use in this invention has two essential functions: (1) to integrate specifically (and stably) at the endogenous presenilin 1 target gene; and (2) to replace a portion of an exon of the endogenous presenilin 1 gene, thereby introducing the human mutation, and the mutation that introduces a new cleavage site in the gene. In a preferred embodiment, a portion of exon 8 is replaced so as to introduce the P264L mutation. Those two essential functions depend on two basic structural features of the targeting vector.

The first basic structural feature of the targeting vector is a pair of regions, known as "arms of homology," which are homologous to selected regions of the endogenous presenilin 1 gene or regions flanking the presenilin 1 gene. This homology causes at least part of the targeting vector to integrate into the chromosome, replacing part (or all) of the presenilin 1 target gene, by homologous recombination.

Homologous recombination, in general, is the rearrangement of DNA segments, at a sequence-specific site (or sites), within or between DNA molecules, through base-pairing mechanisms. The present invention relates to a particular form of homologous recombination sometimes known as "gene targeting."

The second basic structural feature of the targeting vector consists of the actual base changes (mutation(s)) to be introduced into the target gene. In the present invention, the base changes in codon 264 of exon 8, for example, resulted in an amino acid change in amino acid 264 from proline to leucine when the mutated gene was expressed to make protein. Other base changes can be made, as desired, to introduce any of the human mutations listed above into the mammalian genome. The mutation(s) to be introduced into the presenilin 1 target gene is located within the "arms of homology."

Gene targeting, which affects the structure of a specific gene already in a cell, is to be distinguished from other forms of stable transformation, wherein integration of exogenous DNA for expression in a transformed cell is not site-specific, and thus does not predictably affect the structure of any particular gene already in the transformed cell. Furthermore, with the type of targeting vector preferred in the practice of this invention (e.g., the one disclosed below), a reciprocal exchange of genomic DNA takes place (between the "arms of homology" and the target gene), and chromosomal insertion of the entire vector is advantageously avoided.

The examples of this patent disclosure set forth the construction of a presenilin 1 gene targeting vector (and its use) to mutate the murine presenilin 1 protein encoding sequence so that it encodes the murine presenilin 1 protein, containing the human P264L mutation, or any of the other human mutations recited above, and an additional cleavage site. One of ordinary skill in the art will recognize that numerous other targeting vectors can be designed to introduce the same mutations, using the principles of homologous recombination. Gene-targeted, non-human mammals produced using such other targeting vectors are within the scope of the present invention. A discussion of targeting vector considerations follows.

The length of the arms of homology that flank the replacement sequence can vary considerably without significant effect on the practice of the invention. The arms of homology must be of sufficient length for effective heteroduplex formation between one strand of the targeting vector and one strand of a transfected cell's chromosome, at the presenilin 1 target gene locus. Increasing the length of the arms of homology promotes heteroduplex formation and thus targeting efficiency. However, it will be appreciated that the incremental targeting efficiency accruing per additional homologous base pair eventually diminishes and is offset by practical difficulties in target vector construction, as arms of homology exceed several thousand base pairs. A preferred length for each arm of homology is 50 to 10,000 base pairs.

There is considerable latitude in the choice of which regions of the presenilin 1 target gene, i.e., chromosomal regions flanking the presenilin 1 target gene, are represented in the targeting vector's arms of homology. The basic constraint is that the base pairs to be changed in the presenilin 1 target gene must lie within the sequence that constitutes the arms of homology. The arms of homology may lie within the presenilin 1 target gene, but it is not necessary that they do so and they may flank the presenilin 1 target gene.

Preferably, the targeting vector will comprise, between the arms of homology, a positive selection marker. The positive selection marker should be placed within an intron of the target gene, so that it will be spliced out of mRNA and avoid the expression of a target/marker fusion protein. More preferably the targeting vector will comprise two selection markers; a positive selection marker, located between the arms of homology, and a negative selection marker, located outside the arms of homology. The negative selection marker is a means of identifying and eliminating clones in which the targeting vector has been integrated into the genome by random insertion instead of by homologous recombination. Exemplary positive selection markers are neomycin phosphotransferase and hygromycin β phosphotransferase genes. Exemplary negative selection markers are *Herpes simplex* thymidine kinase and diphtheria toxin genes.

To eliminate potential interference on expression of the target protein, the positive selection marker can be flanked by short loxP recombination sites isolated from bacteriophage P1 DNA. Recombination between the two loxP sites at the targeted gene locus can be induced by introduction of cre recombinase to the cells. This results in the elimination of the positive selection marker, leaving only one of the two short loxP sites. (See, U.S. Pat. No. 4,959,317, which is herein incorporated by reference in its entirety). Excision of the positive selectable marker from intron 8 of the mutated presenilin 1 gene can thus be effected.

FIG. 1 illustrates the general principles of gene-targeting for introducing mutations into a mammalian genome using homologous recombination (reviewed in Capecchi, M. R, *Trends Genet.*, 1989, 5, 70–76; Koller and Smithies, *Ann. Rec. Immunol.*, 1992, 10, 705–730). A length of genomic DNA is first depicted by organizing it into regions (numbered 0–5 in FIG. 1*a*). In FIG. 1, several base pair changes (from 1–10) are to be incorporated into the cellular DNA around region 3. Homologous recombination using a gene targeting vector is utilized. The type of gene targeting vector used to incorporate these changes is termed a replacement vector.

As defined previously, a "replacement vector" herein refers to a vector that includes one or more selectable marker sequences and two contiguous sequences of ES cell genomic DNA that flank a selectable marker. These flanking sequences are termed "arms of homology." In FIG. 1*b*, the arms of homology are represented by regions 1–2 and 3–4. The use of DNA derived from the ES cells (isogenic DNA) helps assure high efficiency recombination with the target sequences (te Riele et al., *Proc. Natl. Acad. Sci. USA*, 1992, 89, 5128–5132). The arms of homology are placed in the vector on either side of a DNA sequence encoding resistance to a drug toxic to the ES cells (positive selection marker). A gene encoding susceptibility to an otherwise nontoxic drug (negative selection marker) is placed outside the region of homology. In the replacement vector used in this invention, the positive selection marker is $neo^r$, a gene that encodes resistance to the neomycin analog G418, and the negative selection marker is the herpes simplex virus thymidine kinase gene (HSV-tk) that encodes susceptibility to gancyclovir. When this replacement vector is introduced into ES cells via transfection and its DNA undergoes homologous recombination with ES cellular DNA, the positive selection marker is inserted into the genome between regions 2 and 3 in this example (making the transformed cells resistant to G418) while the negative selection markers is excluded (making the cells resistant to gancyclovir). Thus, to enrich for homologous recombinants, transfected ES cells are grown in culture medium containing G418 to select for the presence of the $neo^r$ gene and gancyclovir to select for the absence of the HSV-TK gene. Preferably, the positive selection marker is eliminated by using, for example, cre/lox technology once the mammal is crossed with another mammal.

If base pair changes (mutations) are introduced into one of the arms of homology it is possible for these changes to be incorporated into the cellular gene as a result of homologous recombination. Whether or not the mutations are incorporated into cellular DNA as a result of homologous recombination depends on where the crossover event takes place in the arm of homology bearing the changes. For example, as depicted by scenario "A" in FIG. 1, the crossover in the arm occurs proximal to the mutations and so they are not incorporated into cellular DNA. In scenario "B", the crossover takes place distal to the position of the mutations and they are incorporated into cellular DNA. Because the location of the crossover event is random, the frequency of homologous recombination events that include the mutations is increased if they are placed closer to the positive selection marker.

By the above method, the skilled artisan can achieve the incorporation of the selectable marker at a preselected location in the gene of interest flanked by specific base pair changes. Presumably, the artisan would preferably choose to have the selectable marker incorporated within the intron of the gene of interest so as not to interfere with endogenous gene expression while the mutations would be included in adjacent coding sequence so as to make desired changes in the protein product of interest (FIG. 1), (Askew et al., *Mol. Cell. Biol.*, 1993, 13, 4115–4124, Fiering et al., *Proc. Natl. Acad. Sci. USA*, 1993, 90, 8469–8473; Rubinstein et al., *Nuc. Acid Res.*, 1993, 21, 613–2617, Gu et al., *Cell*, 1993, 73, 1155–1164, and Gu et al., *Science*, 1994, 265, 103–106).

Thus, in the manner described above, a gene-targeted, non-human mammal comprising a human PS-1 mutation is prepared. The mammal can be heterozygous (contains one copy of the human PS-1 mutation) or homozygous (contains two copies of the human PS-1 mutation). In a preferred embodiment, a mouse is prepared which is PS-1$^{P264L/+}$ (heterozygous) or PS-1$^{P264L/P264L}$ (homozygous).

The gene-targeted, non-human mammals comprising a human PS-1 mutation described above can be crossed with mammals having a Swedish FAD mutation and "humanized" Aβ sequence in the APP gene (e.g., APP$^{NLh/NLh}$ mouse) to produce mammals referred to as APP$^{NLh/NLh}$×PS-1$^{P264L/P264L}$, APP$^{NLh/+}$×PS-1$^{P264L/P264L}$, APP$^{NLh/+}$×PS-1$^{P264L/+}$ or APP$^{NLh/NLh}$×PS-1$^{P264L/+}$. In addition, the gene-targeted, non-human mammals comprising a human PS-1 mutation described above can be crossed with mammals having a Swedish APP695 mutation (e.g., Tg2576 mouse). Prior to crossing such mammals, however, it is preferred to remove the positive selection marker, such as neo$^r$, using cre/lox technology.

The present invention is also directed to a method for identifying a compound for treating Alzheimer's disease. A compound is administered to a mammal that is heterozygous or homozygous for a mutation of the PS-1 gene and also contains a human Swedish APP695 mutation, or generational offspring thereof, or to a mammal heterozygous or homozygous for a mutation of the PS-1 gene, a human FAD Swedish mutation, and a humanized Aβ mutation, and generational offspring thereof. Any compound to be tested can be administered in a variety of amounts by any variety of routes including, but not limited to, intravenously, orally, direct injection in the brain, and the like. A tissue sample from the mammal including, but not limited to, brain tissue, non-brain tissue and body fluids (e.g. blood and plasma) is obtained and the amount of Aβ peptide in the tissue sample is measured. A decrease in the amount of Aβ peptide in the tissue sample is indicative of a compound that can be used to treat Alzheimer's disease.

The present invention is also directed to a method of treating an individual suspected of having Alzheimer's disease. An individual suspected of having Alzheimer's disease is any human having been examined by a physician and diagnosed as having Alzheimer's disease or symptoms thereof. A compound identified by the methods described above relating to a mammal that is heterozygous or homozygous for a mutation of the PS-1 gene and also contains a human Swedish APP695 mutation, or generational offspring thereof, or to a mammal that is heterozygous or homozygous for a mutation of the PS-1 gene, a human FAD Swedish mutation, and a humanized Aβ mutation, and generational offspring thereof, is administered to the individual in an amount effective to decrease the amount of Aβ peptide in the brain of the individual. An amount effective to decrease the amount of Aβ peptide can be determined from the identification process of the compound using a mammal that is heterozygous or homozygous for a mutation of the PS-1 gene and also contains a human Swedish APP695 mutation, or generational offspring thereof, or using a mammal that is heterozygous or homozygous for a mutation of the PS-1 gene, a human FAD Swedish mutation, and a humanized Aβ mutation, or generational offspring thereof, as a starting amount and scaling up for use in humans as is well known to those skilled in the art. An effective Alzheimer's disease treatment amount is an amount of a compound that measurably reduces the physiological pathology of Alzheimer's disease or an amount that reduces the physical manifestations or symptoms of Alzheimer's disease. One skilled in the art can, for example, begin with an amount of a compound that decreases the amount of Aβ peptide in the brain, as described above, and can scale up or down the amount depending on the desired effect and the effect achieved in a particular individual.

The present invention is also directed to compounds that are identified by the screening methods described above. The compounds can be any identifiable chemical or molecule, including, but not limited to, a small molecule, a peptide, a protein, a sugar, a nucleotide, or a nucleic acid, and such compound can be natural or synthetic.

In order that the invention disclosed herein may be more efficiently understood, examples are provided below. It should be understood that these examples are for illustrative purposes only and are not to be construed as limiting to the invention in any manner. Throughout these examples, molecular cloning reactions, and other standard recombinant DNA techniques, were carried out according to methods described in *Maniatis et al., Molecular Cloning—A Laboratory Manual*, 2$^{nd}$ed., Cold Spring Harbor Press (1989) (hereinafter, "Maniatis et al."), using commercially available enzymes, except where otherwise noted.

EXAMPLES

Example 1

Cloning of Mouse PS-1 Exon 8 Region

Figure 2:
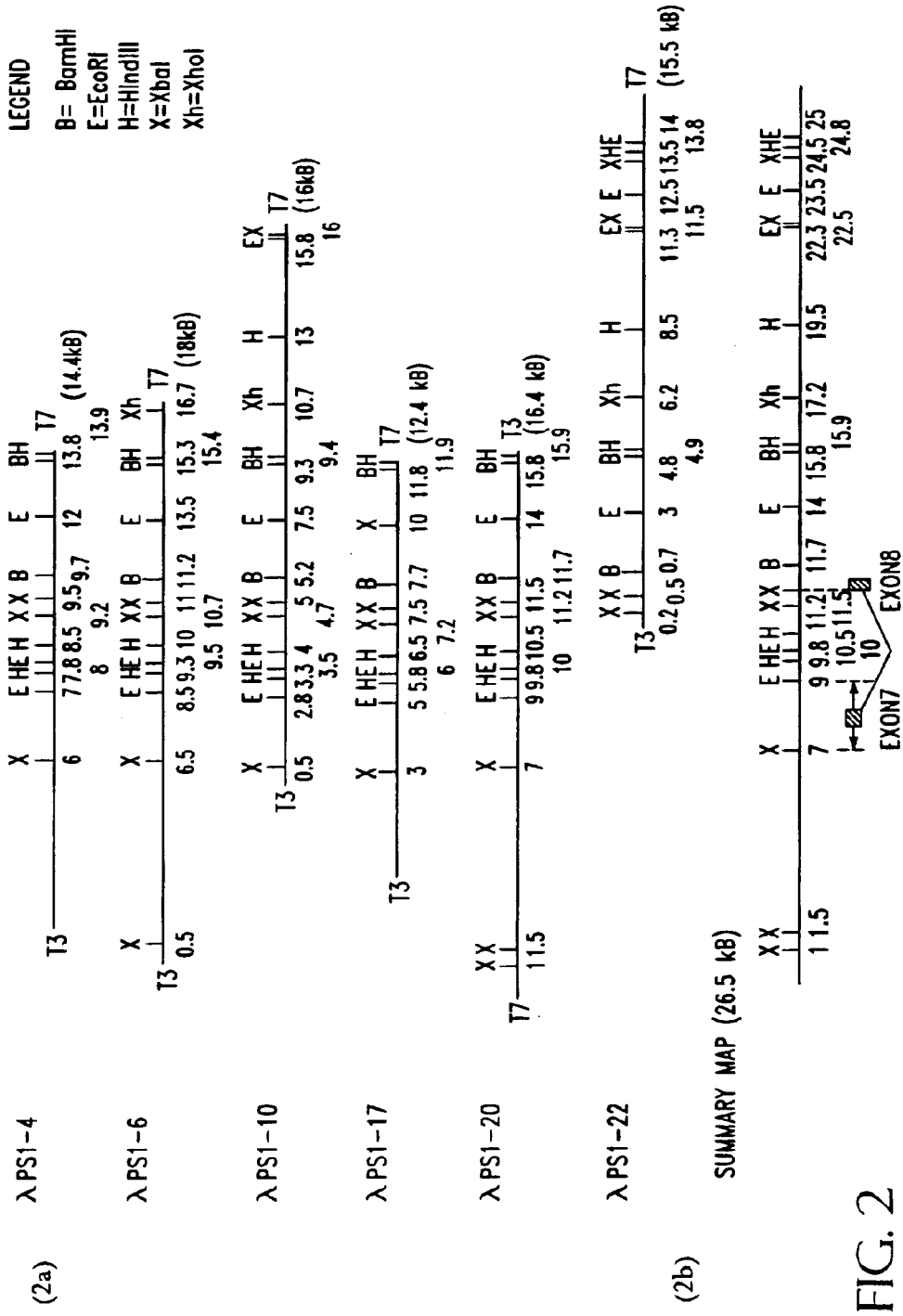
FIG. 2 is a set of mouse PS-1 genomic clone maps prepared using the Flash™ Non-radioactive Gene Mapping Kit. Letter abbreviations for restriction endonucleases are as follows: E, EcoRI; X, XbaI; H, HindIII; B, BamHI; Xh, XhoI.

The mouse PS-1 genomic DNA was cloned from a bacteriophage library created from 129/Sv mouse DNA partially digested with Sau3A and into the BamHI site of Lambda DASH™II (Reaume et al., *Science*, 1995, 267, 1831–1833, which is incorporated herein by reference in its entirety). Using standard molecular biology techniques (Maniatis et al.), approximately $1.2 \times 10^6$ recombinant bacteriophages were screened for the presence of PS-1 sequences by hybridization with a small, radiolabeled PS-1 specific DNA probe. This 477 base pair PS-1 probe was generated by polymerase chain reaction (PCR) amplification (Mullis et al., *Methods Enzymol.*, 1987, 155, 335–350) of mouse genomic DNA using primers R892 (CTC ATC TTG GCT GTG ATT TCA; SEQ ID NO:1) and R885 (GTT GTG TTC CAG TCT CCA; SEQ ID NO:2) which hybridize to the 3' end of exon 7 and the 5' end of exon 11 respectively (FIG. 2). The amplified fragment was separated from other components of the reaction by electrophoresis on a 1.0% agarose gel, and purified using GeneClean®II (Bio 101, Inc., La Jolla, Calif.). Purified probe DNA was radioactively labeled with $^{32}$P-dCTP by the random primer method using materials and methods supplied by the kit manufacturer (Multiprime DNA Labeling System; Amersham Life Sciences, Arlington Heights, Ill.).

From this screen, 13 clones were identified that hybridized to the PS-1 probe. The clones were identified as: λPS1-4, λPS1-5, λPS1-6, λPS1-10, λPS1-11, λPS1-17, λPS1-19, λPS1-20, λPS1-22, λPS1-24, λPS1-28, λPS1-31, and λPS1-35. These clones were purified by limiting dilution and plaque hybridization with the PS-1 probe (Maniatis et al.).

From each clone, DNA was prepared from bacteriophage particles purified on a CsCl gradient (Maniatis et al.).

Figure 3:
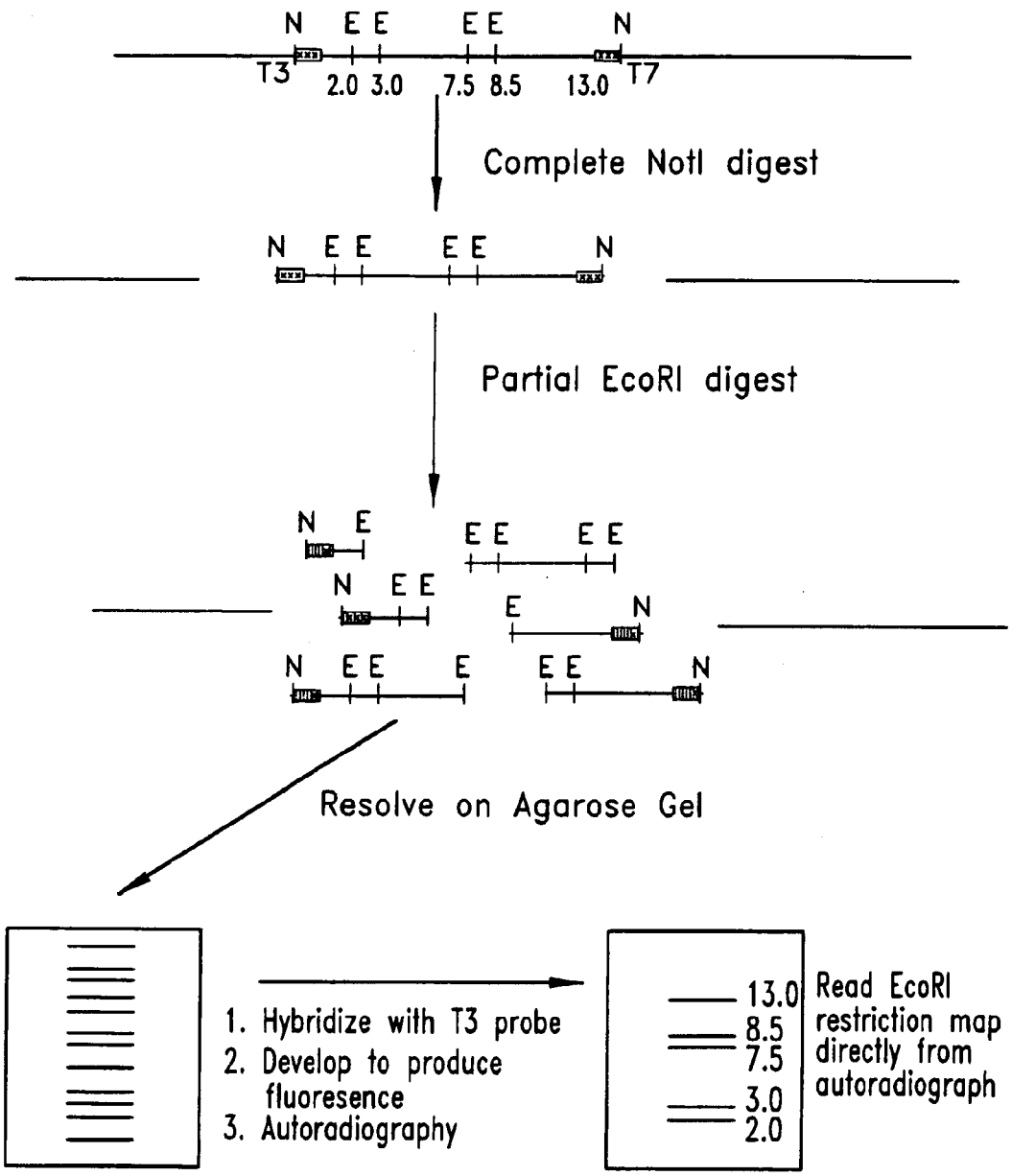
FIG. 3 is a representative restriction map used to illustrate a Flash™ restriction mapping method.

Restriction maps were then generated for each of the cloned inserts using the FLASH™ Non-radioactive Gene Mapping Kit (Stratagene® Inc., La Jolla, Calif.). A typical restriction map generated by this method is illustrated in FIG. 3. This method of restriction enzyme mapping involves first completely digesting 10 µg of the bacteriophage DNA with the restriction enzyme NotI using standard restriction enzyme digest conditions (Maniatis et al.). NotI cuts all clones in the vector DNA at either end of the cloned insert so as to leave a T3 bacteriophage promoter attached to one end of the insert and a T7 bacteriophage promoter attached to the other end. The NotI digested DNA is then partially digested with the enzyme EcoRI, as an example, using limiting amounts of enzyme (0.2 units/µg DNA) in an 84 µl reaction volume at 37° C. Aliquots (26 µl) were removed after 3 minutes, 12 minutes and 40 minutes and the digest reaction was stopped by the addition of 1 µl of 0.5 M EDTA. DNA from all three time points was resolved on a 0.7% agarose gel, visualized by ethidium bromide staining, and then transferred to a GeneScreen Plus® membrane (NEN® Research Products, Boston, Mass.) by capillary transfer (Maniatis et al., supra). The membrane was hybridized with an alkaline phosphatase labeled oligonucleotide that was specific for the T3 promoter (supplied with the FLASH™ kit) using reagents and methods supplied by the kit manufacturer. After hybridization, the membrane was washed and developed with a chemiluminescent-yielding substrate and then exposed to X-ray film in the dark for approximately 60 minutes.

The oligonucleotide probes effectively label one end of the insert. By determining the positions of the bands on the X-ray film and calculating the DNA size to which they corresponded, it was possible to determine the position of the EcoRI sites relative to the T3 end of the insert (FIG. 3). These results could then be complemented by stripping the probe off of the membrane, and rehybridizing with a T7-specific oligonucleotide in order to determine the positions of the EcoRI sites relative to the T7 end of the insert. This process was repeated using the enzymes HindIII and XbaI. By comparing the restriction enzyme maps of the different overlapping clones a composite map was assembled. Of the 13 original clones isolated, 6 independent clones were identified (FIG. 2).

Figure 4:
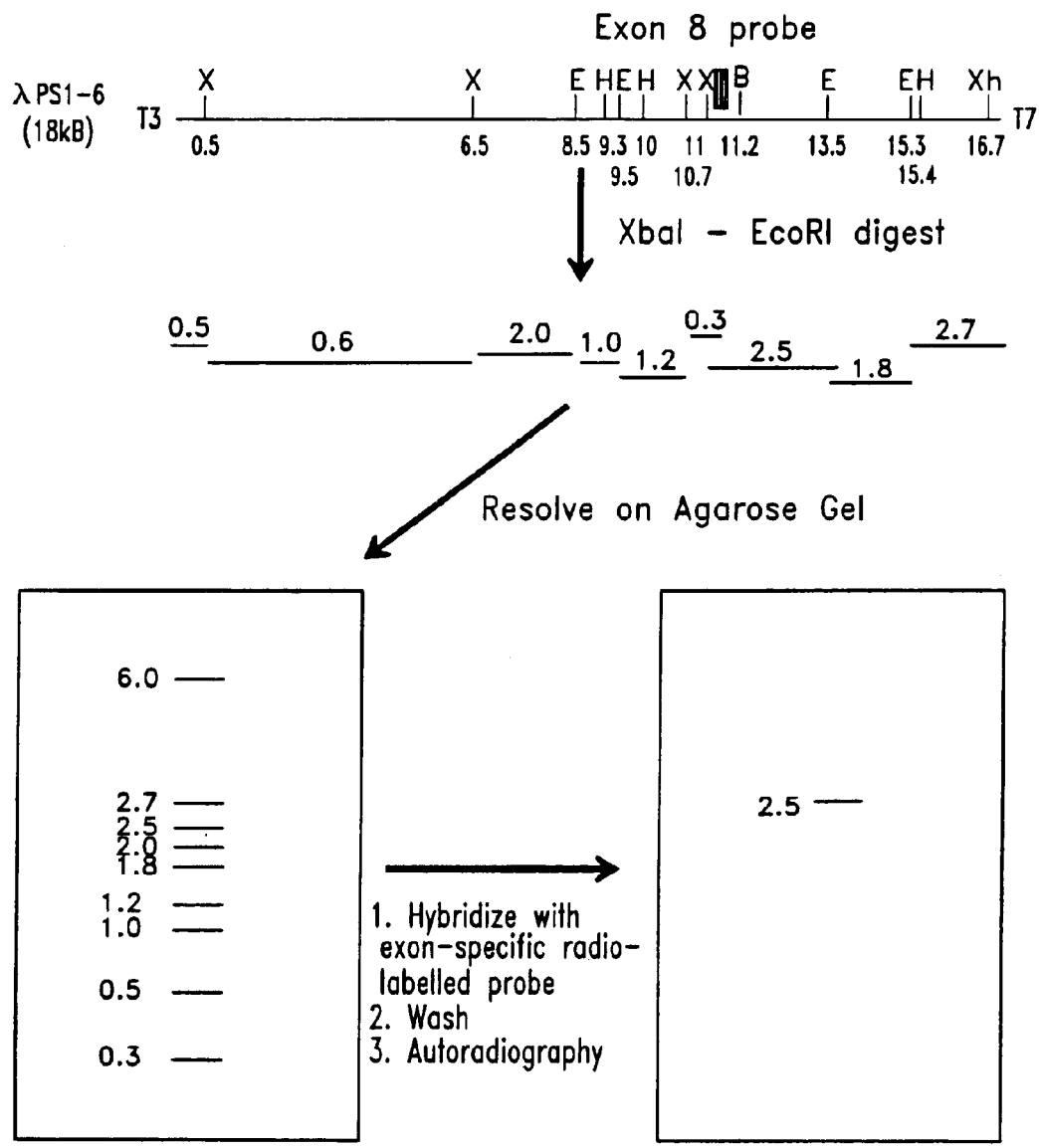
FIG. 4 is a diagram illustrating the strategy for placing exons 7 and 8 on the restriction map of PS-1.

Exon 8 was located on the restriction map hybridizing exon-specific probes to complete digests of each of the 6 different lambda genomic clones. Initially, 3 µg of DNA from each of the 6 different clones was completely digested with the restriction enzymes EcoRI and XbaI. The digested DNA was resolved on a 0.8% agarose gel, visualized by means of ethidium bromide staining and transferred to a GeneScreen Plus® membrane by capillary transfer. The membrane was then hybridized with a DNA probe that specifically hybridized to sequences from mouse PS-1 exon 8. This probe was generated by PCR using oligonucleotides FEX8 (ATT TAG TGG CTG TTT TGT G; SEQ ID NO:3) and REX8 (AGG AGT AAA TGA GAG CTG GA; SEQ ID NO:4) which hybridize to the 5' and 3' ends of exon 8, respectively. After hybridization, the membrane was washed and exposed to X-ray film (FIG. 4). This experiment revealed that all clones contained a 2.5 kb fragment that hybridized to the exon 8 probe. By combining this information with the restriction map data for each lambda clone, exon 8 was identified on the map (position 11.5 to 14 on the summary map, FIG. 2).

A similar procedure was used to identify the position of exon 7 on our composite map using exon 7-specific probe and utilizing the restriction enzymes XbaI and EcoRI. The exon 7-specific probe was generated using PCR primers F892 (TGA AAT CAC AGC CAA GAT GAG; SEQ ID NO:5) and PS1-1(GCA CTC CTG ATC TGG AAT TTT G; SEQ ID NO:6). Exon 7 was localized to the 2 kb XbaI-EcoRI fragment of all clones except λPS1-22 which allowed for the determination that exon 7 is located between positions 7.0 and 9.0 on the summary map (FIG. 2).

Exon-specific probes were also used to obtain additional restriction map information using additional restriction enzymes. For example, when λPS1-22 was digested with NotI and BamHI, resolved on an agarose gel, transferred to a Genescreen Plus® membrane and probed with the exon 8-specific probe, a 700 bp fragment was identified. This information, when combined with the information from the other bacteriophage clones, allowed placement of the BamHI at position 11.7 on the composite map (FIG. 2). This process was repeated for the restriction enzyme XhoI.

Cloning of additional regions of the mouse PS-1 gene can also be accomplished, as desired, in order to prepare additional vectors comprising other human mutations.

Example 2

Construction of a Replacement Vector

Figure 5:
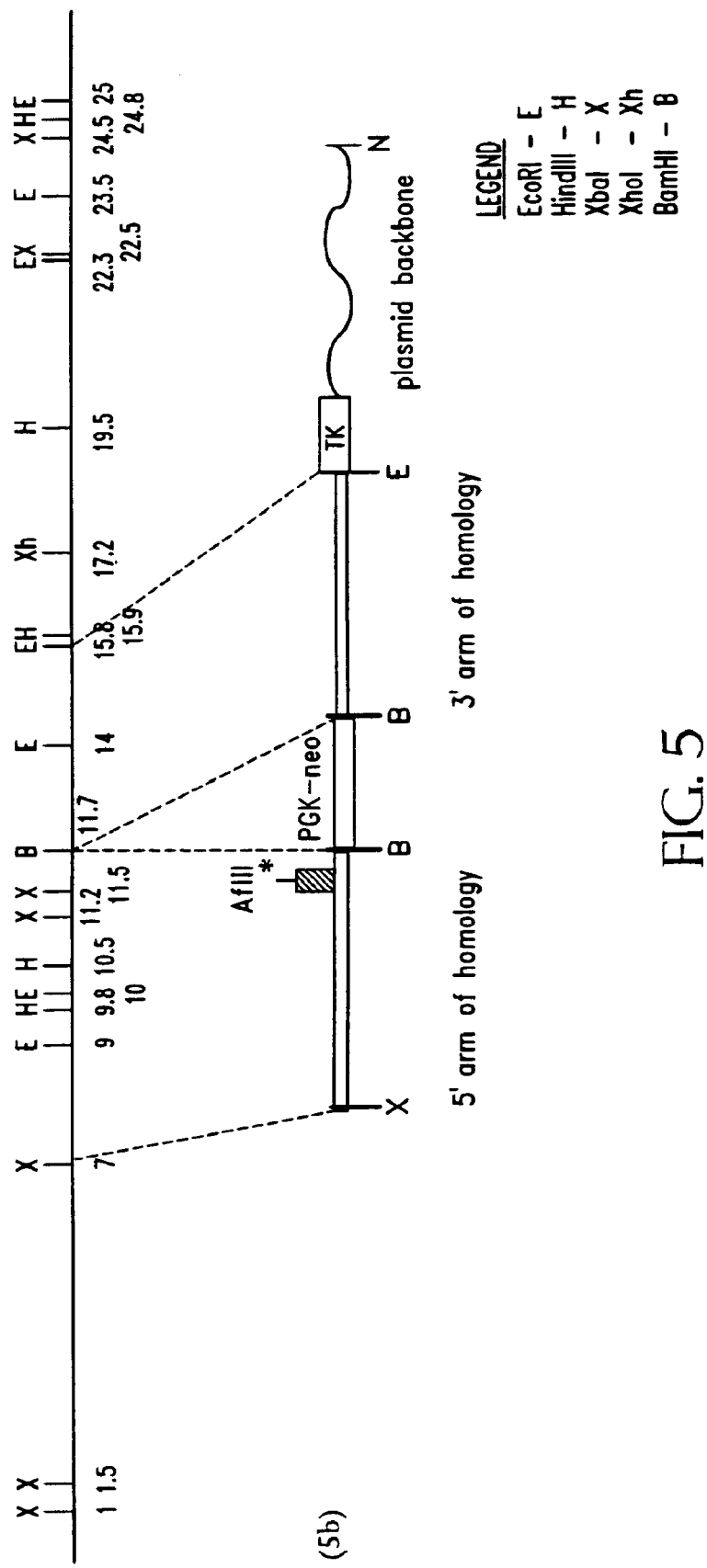
FIG. 5 is a pair of genetic maps illustrating the relationship between Exon 8 of PS-1 and the pPS1–8-TV replacement vector, Letter abbreviations for restriction endonucleases are as follows: E, EcoRI; X, XbaI; H, HindIII; B, BamHI; Xh, XhoI, N, NotI.

A 4.7 kb XbaI-BamHI fragment (which also contains two internal XbaI fragments) located at positions 7.0 to 11.7 on the summary map (FIG. 2), was chosen as the 5' arm that included the necessary mutations and a 4.1 kb BamHI-EcoRI fragment (which also contains an internal EcoRI site) located at positions 11.7 to 15.8 on the summary map (FIG. 2), as a 3' arm. These fragments were isolated first and cloned into pBlueScript® SK+ (Stratagene Cloning Systems, La Jolla, Calif.) and then further subcloned into the plasmid pPNTIox$^2$ (described below) that contained a neo$^r$ gene, an HSV-TK gene and linker sequences to produce a replacement vector (pPS1-8-TV, FIG. 5) with the same general structure as that discussed above.

Figure 6:
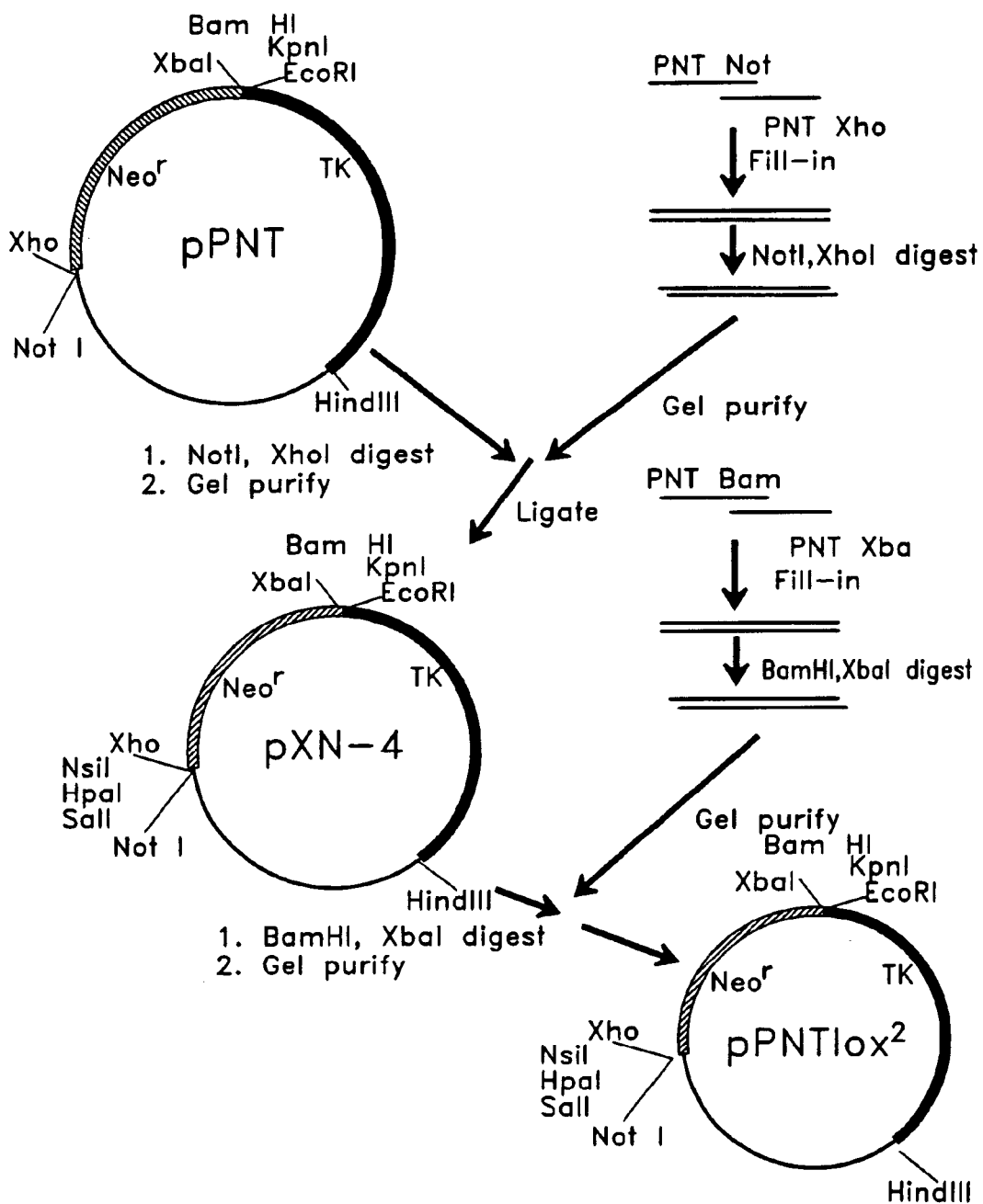
FIG. 6 is a schematic diagram illustrating the construction of plasmid pPNTIox$^2$.

(a) Construction of the Intermediate Plasmid pPNTIox$^2$ pPSI-8-TV was created from pPNT (Tybulewicz et. al., Cell, 1991, 65, 1153–1163; obtained from Dr. Richard Mulligan, MIT) by first inserting two oligonucleotide linkers on each side of the neo$^r$ cassette creating the intermediate called pPNTIox$^2$ (FIG. 6). A double-stranded 79 base pair 5' linker was created by annealing two single-stranded oligonucleotides that overlap at their 3' ends and then filling in the remaining single-stranded regions with the Klenow fragment of DNA polymerase I. The oligonucleotides PNT Not (GGA AAG AAT GCG GCC GCT GTC GAC GTT AAC ATG CAT ATA ACT TCG TAT; SEQ ID NO:7) and PNT Xho (GCT CTC GAG ATA ACT TCG TAT AGC ATA CAT TAT ACG AAG TTA TAT GC; SEQ ID NO:8) (150 ng of each) were combined in a 30 µl reaction mixture containing 5 U of Klenow polymerase, Klenow polymerase buffer and 2 mM dNTPs (dATP, dCTP, dGTP, and dTTP). After incubating for 1 hour at 37° C., a portion (5 µl) of this reaction mixture was simultaneously digested with the restriction enzymes NotI and XhoI to liberate the restriction enzyme sites at each end of the linker. In addition, 200 ng of pPNT was digested with NotI and XhoI. The digested plasmid was resolved on a 0.8% agarose gel, purified from the gel, and treated with calf intestinal phosphatase according to standard methods (Maniatis et al.). A quantity (66 ng) of the double digested linker was ligated to the double-digested and phosphatase-treated pPNT DNA (Maniatis et al). Following DNA transformation of competent WM 1100 E. coli (Dower, Nucleic Acids Res., 1988, 16, 6127–6145), plasmid DNA was isolated from ampicillin-resistant bacteria (Holmes et al., Anal. Biochem., 1981, 114, 193–197) and analyzed by restriction enzyme analysis. The proper recombinant plasmids were identified as having acquired SalI, HpaI and NsiI sites (present in the linker) while still retaining the NotI and XhoI sites of the starting plasmid. One such recombinant plasmid with a 79 bp linker sequence was identified and called pXN-4 (FIG. 6).

A similar approach was used to insert a 3' linker between the XbaI and BamHI sites of pXN-4. The oligonucleotides used to synthesize the linker were PNT Xba (CGT TCT AGA ATA ACT TCG TAT AAT GTA TGC TAT; SEQ ID NO:9) and PNT Bam (CGT GGA TCC ATA ACT TCG TAT AGC ATA CAT TAT; SEQ ID NO:10). In this case, pXN-4 and the double-stranded linker DNA were digested with XbaI and BamHI. The purified fragments were joined by DNA ligation and transformed into competent WM1100 bacteria. Plasmid DNA was digested with XbaI and BamHI, end-labeled with $^{32}$P-dCTP and Klenow polymerase, and resolved on an 8% acrylamide gel (Maniatis et al.). The gel was dried and exposed to X-ray film. Proper recombinant clones were identified by the presence of a 40 base pair band liberated by the XbaI-BamHI double digest. The resulting plasmid was designated "pPNTIox$^2$" (FIG. 6).

To confirm the sequences of the inserted linkers, a fragment containing both linkers was isolated from pPNTIox$^2$ using NotI and EcoRI and cloned into pBlueScript® SK+, a vector that was more amenable to nucleotide sequencing. Identity of the linkers was confirmed by direct nucleotide sequencing (Sanger, *Proc. Natl. Acad. Sci. USA*, 1977, 74, 5463–5467) using T3 and T7 sequencing primers (Stratagene® Inc., La Jolla, Calif.) and Sequenase Version 2.0 DNA Sequencing Kit (United States Biochemical, Cleveland, Ohio).

(b) Subcloning Arms of Homology.

Figure 7:
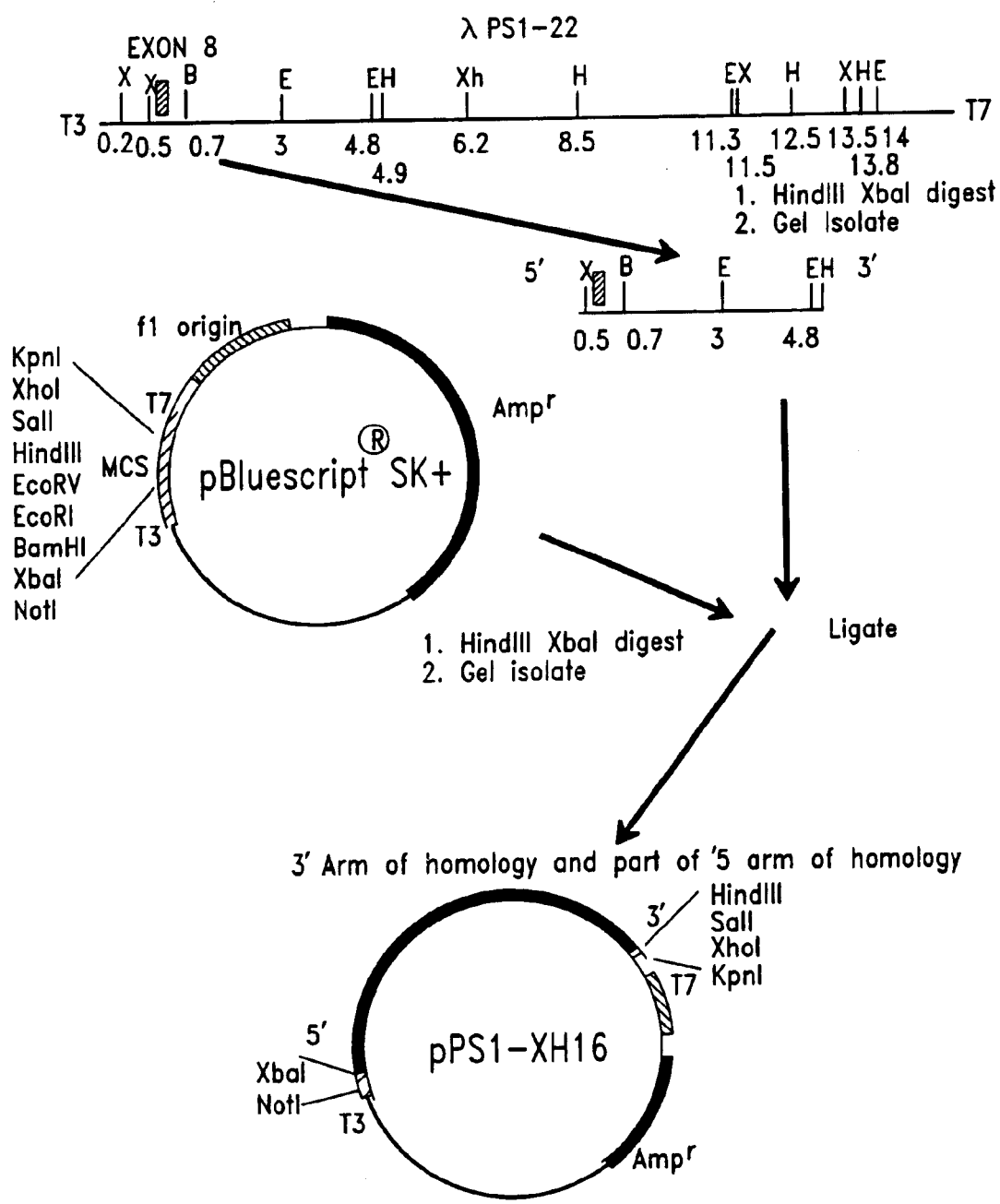
FIG. 7 is a schematic diagram illustrating the construction of plasmid pPS1-XH16.

An XbaI-HindIII fragment positions 11.5 to 15.9 on the summary map, FIG. 2) containing the 3' arm of homology and the fragment used for in vitro mutagenesis was first isolated from λPS1-22 by digesting 30 μl of the phage DNA with XbaI and HindIII, resolving the digested DNA on a 0.8 agarose gel, visualizing the DNA with ethidium bromide staining and then excising the 4.4 kb fragment from the gel. DNA was purified from the gel using GeneClean® II (Bio 101 Inc., La Jolla, Calif.). Simultaneously, 1 μg of pBlue-Script® SK+ was digested with XbaI and HindIII and subsequently purified by the same procedure. Approximately 400 ng of the purified lambda DNA and 100 ng of the purified plasmid DNA were combined in a 10 μl ligation reaction. Following transformation of competent WM 100 *E. coli*, plasmid DNA was isolated from ampicillin-resistant bacteria and analyzed by restriction enzyme analysis to identify the resultant plasmids (FIG. 7). In this case, plasmid DNA from transformed bacteria was first analyzed by digesting it with XbaI and HindIII in order to determine whether the plasmid DNA had acquired the 4.4 kb PS-I fragment. This plasmid was designated "pPS I-XH16."

Figure 8:
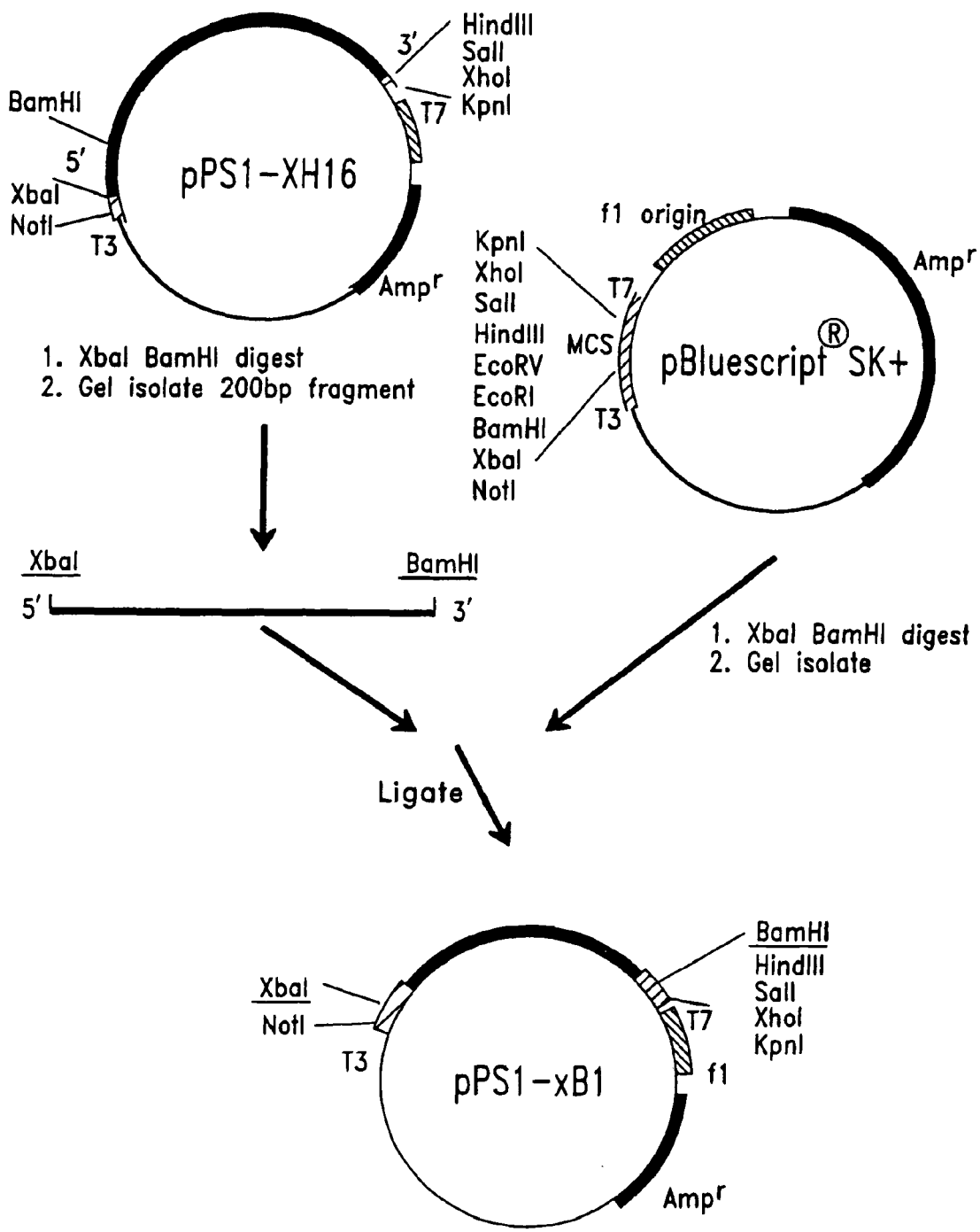
FIG. 8 is a schematic diagram illustrating the construction of plasmid pPS1-XB1.

Similar procedures were used to isolate a 200 bp XbaI-BamHI fragment from pPS1-XH16 and subclone it into pBlueScript® SK+. The resulting plasmid was designated "pPS1-XB1" (FIG. 8).

Figure 9:
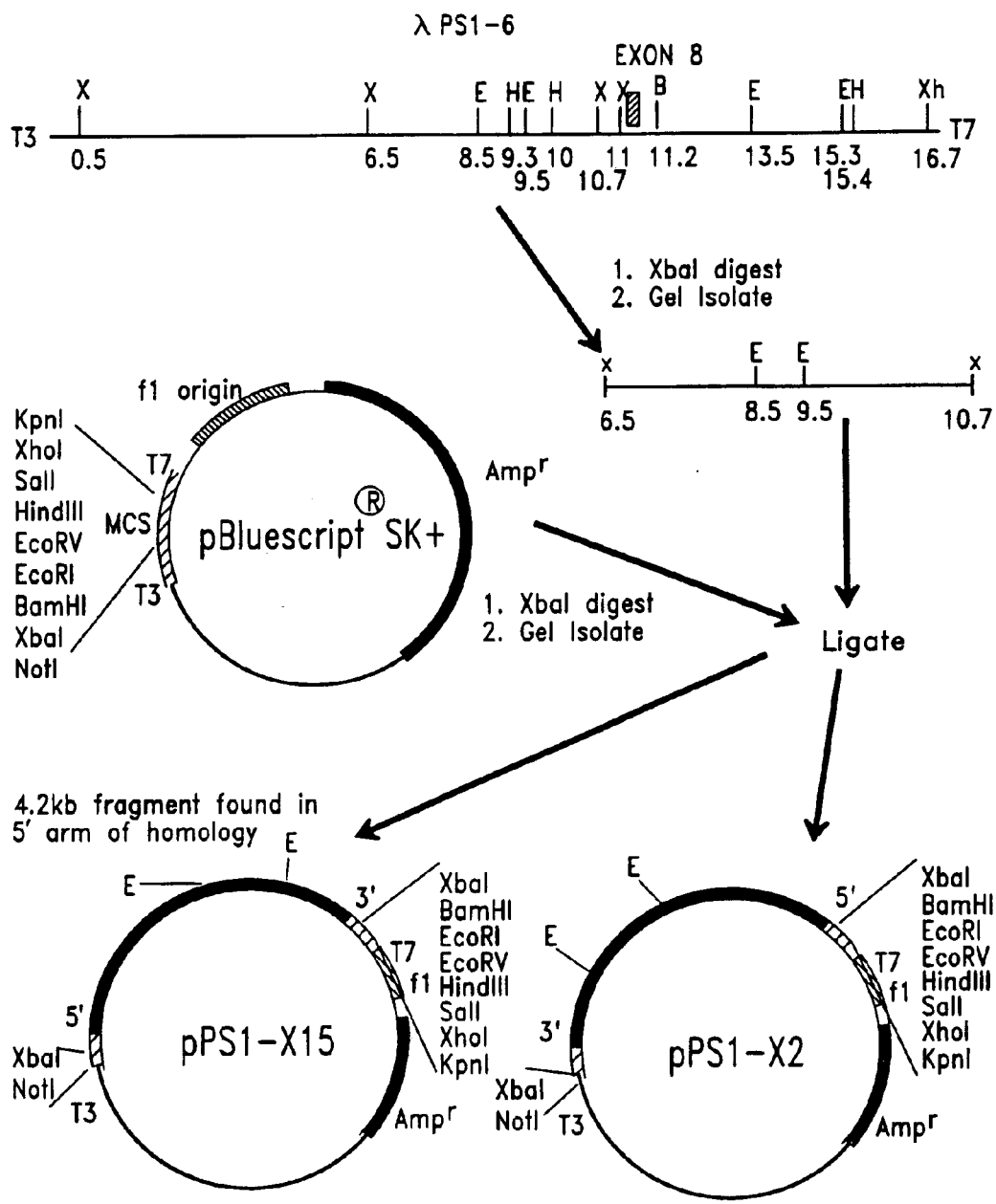
FIG. 9 is a schematic diagram illustrating the construction of plasmids pPS1-X15 and PS1-X2.

One of the fragments in the 5' arm of homology (a 4.2 kb XbaI fragment at positions 7.0 to 11.2 on summary map; FIG. 2) was similarly subcloned from λPS1-6 into pBlue-Script® SK+ and designated "pPS1-X15" (FIG. 9). Because this insert could be positioned in the plasmid in either of two orientations, plasmid DNA was further screened by digesting it with the enzyme EcoRI. In this way, it was determined that the clone pPS1-X15 had the PS-1 insert oriented such that the 5' end was closest to the T3 promoter while in pPS1-X2 the 5' end was adjacent to the T7 promoter (FIG. 9).

Figure 10:
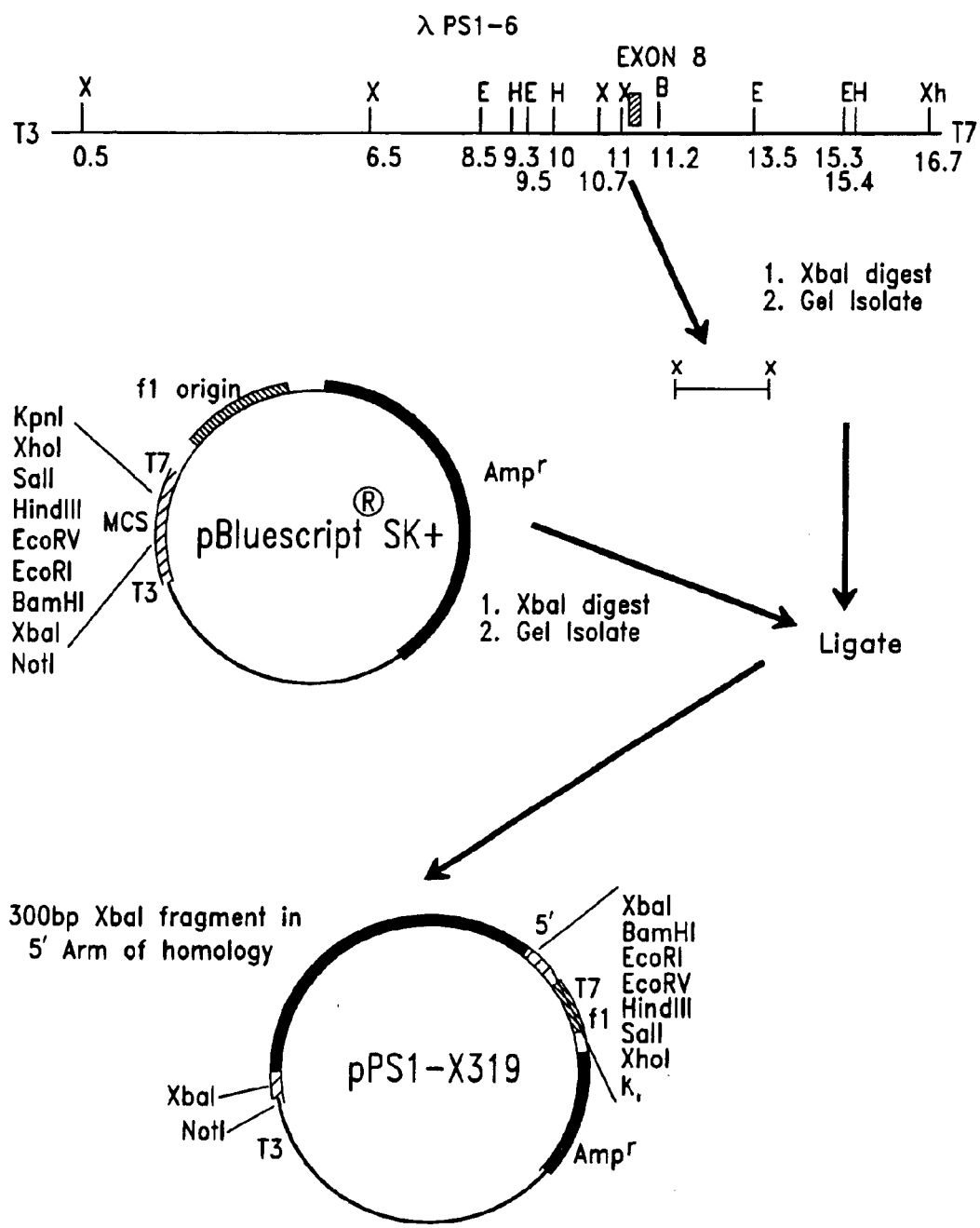
FIG. 10 is a schematic diagram illustrating the construction of plasmid pPS1-X319.

The 300 bp XbaI fragment in the 5' arm (position 11.2 to 11.5 on summary map; FIG. 2) was also similarly cloned into pBlueScript® SK+ from λPS1-20 and named pPS1-X319 (FIG. 10). In this case, the orientation of the XbaI fragment was not determined by subsequent restriction mapping.

(c) Restriction Mapping Arms of Homology.

Figure 11:
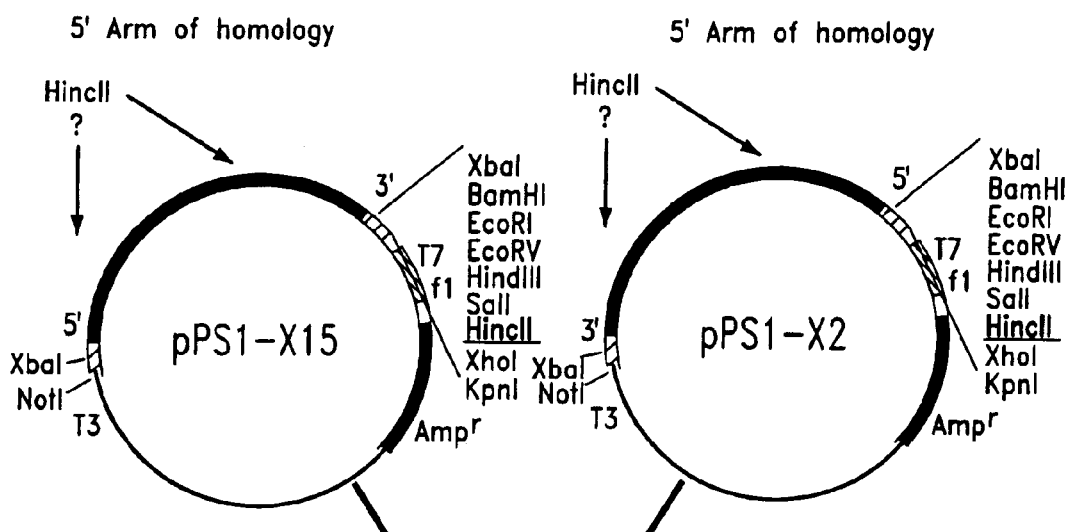
FIG. 11 is a schematic diagram illustrating the restriction mapping of the 5' Arm of Homology from plasmids pPS1-X15 and pPS1-X2.
Figure 11:
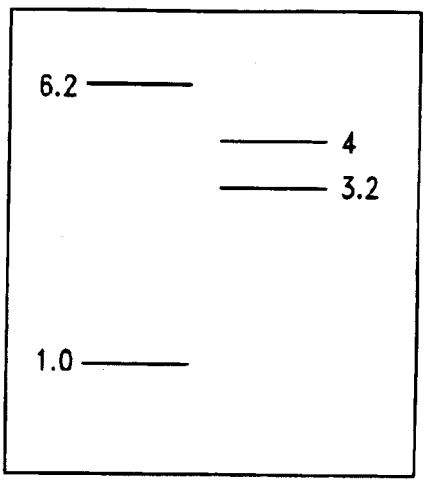
Figure 11:
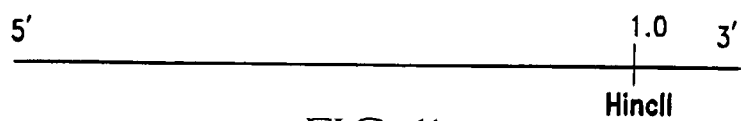

Further restriction enzyme mapping was performed on the pPS1-X315 and pPS1-X2. As an example, each of the two plasmids were digested with the enzyme HincII, resolved on an agarose gel, and visualized with ethidium bromide. Because a HincII site is known to exist in the pBlueScript® SK+ plasmid backbone within the multiple cloning site region near the T7 promoter relative to the insert position, it was possible to determine the position of the HincII site in the 4.2 PS-1 fragment by determining the fragment sizes in each of the two digested samples (FIG. 11).

Figure 12:
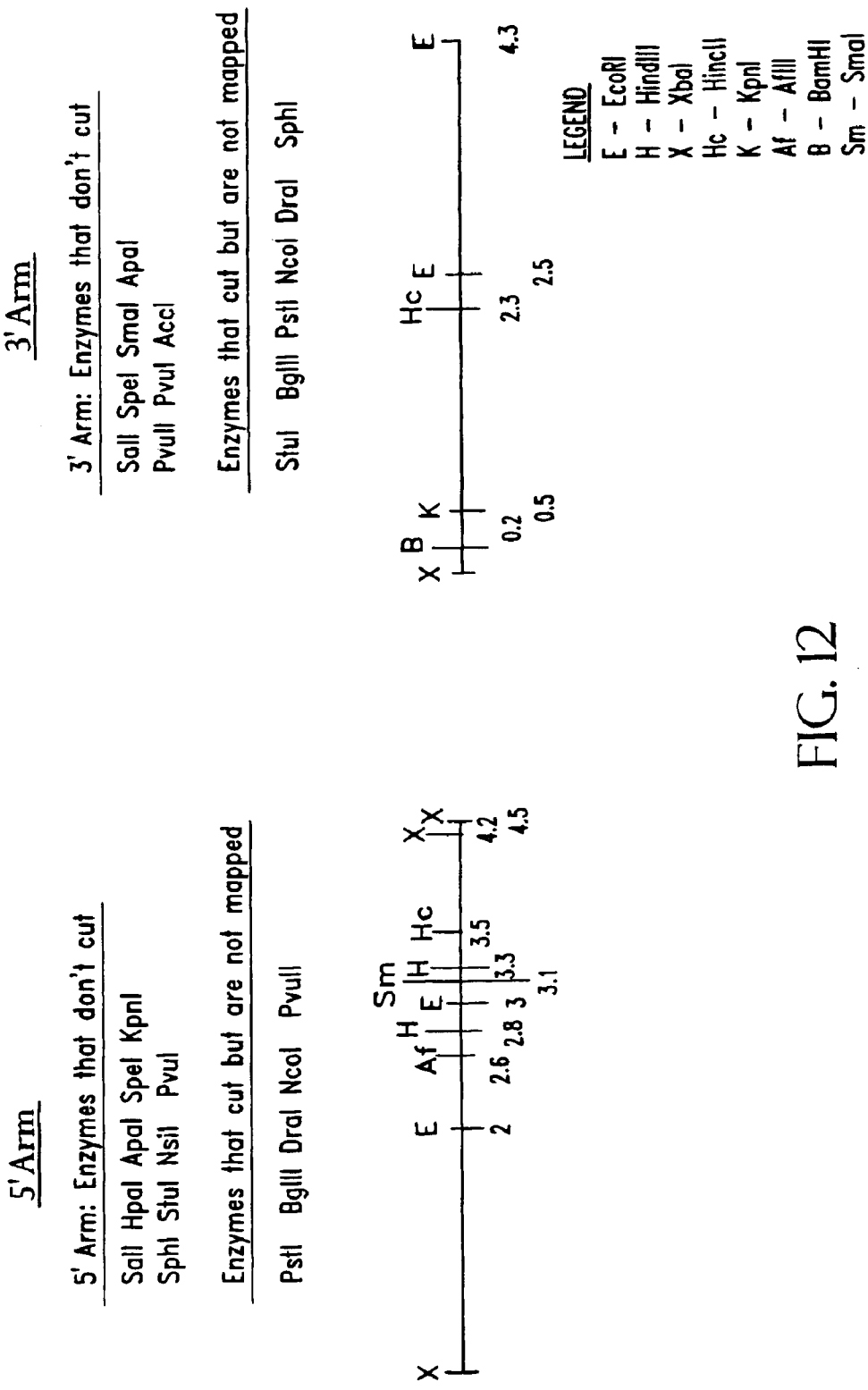
FIG. 12 is a pair of restriction maps for the PS1 3' and 5' arms of homology.

Positions of restriction enzymes sites that occurred once or twice in the 4.2 kb PS-1 fragment were determined by the above method. If more than two sites of a given enzyme were present, it became necessary to determine the relative positions by double-digesting each of the two plasmids with the enzyme in question as well as an additional enzyme which cut at sites capable of resolving ambiguities. In many cases, enzymes that cut more than twice were not resolved in this way but simply noted as having multiples sites in the 4.2 kb PS-1 fragment. The list of additional enzymes used to characterize this region include, but are not limited to, AccI, ApaI, BamHI, EcoRI, HincII, HpaI, KpnI, NsiI, PstI, SalI, SmaI, SpeI, and XhoI. A summary of these data is illustrated in FIG. 12. The same procedures were used to create a restriction enzyme map for the pPS1-XH16 (FIG. 12).

(d) Mutagenesis of the 3' Arm of Homology.

Figure 13:
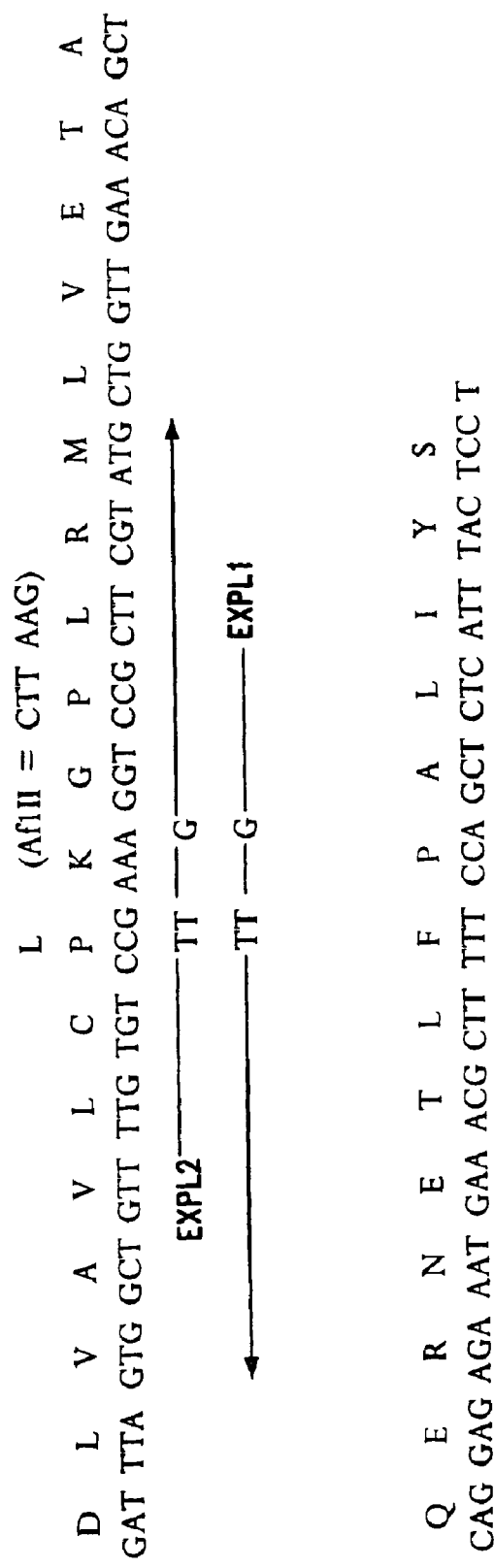
FIG. 13 is a partial sequence of exon 8 of PS-1 illustrating the base changes to effect the P264L mutation and the addition of the AflII restriction endonuclease site of this invention.

A total of 3 base pair changes were introduced into the exon 8 region using a PCR strategy (for summary of changes, see FIG. 13). The P264L mutation, and an AflII site were introduced. Ten ng of pPS1-XB1 were included into each of two PCR reactions. The first reaction contained the primers EXPL2 (TTG TGT CTT AAG GGT CCG CTT CGT ATG; SEQ ID NO:11) and T7 (Stratagene Cloning Systems, La Jolla, Calif.). This generated a 220 bp band that encompassed the 3' end of exon 8 and clone PS1-XB1. This fragment also included the P264L mutation and a novel AflII site that resulted as part of the P264L change.

Figure 14:
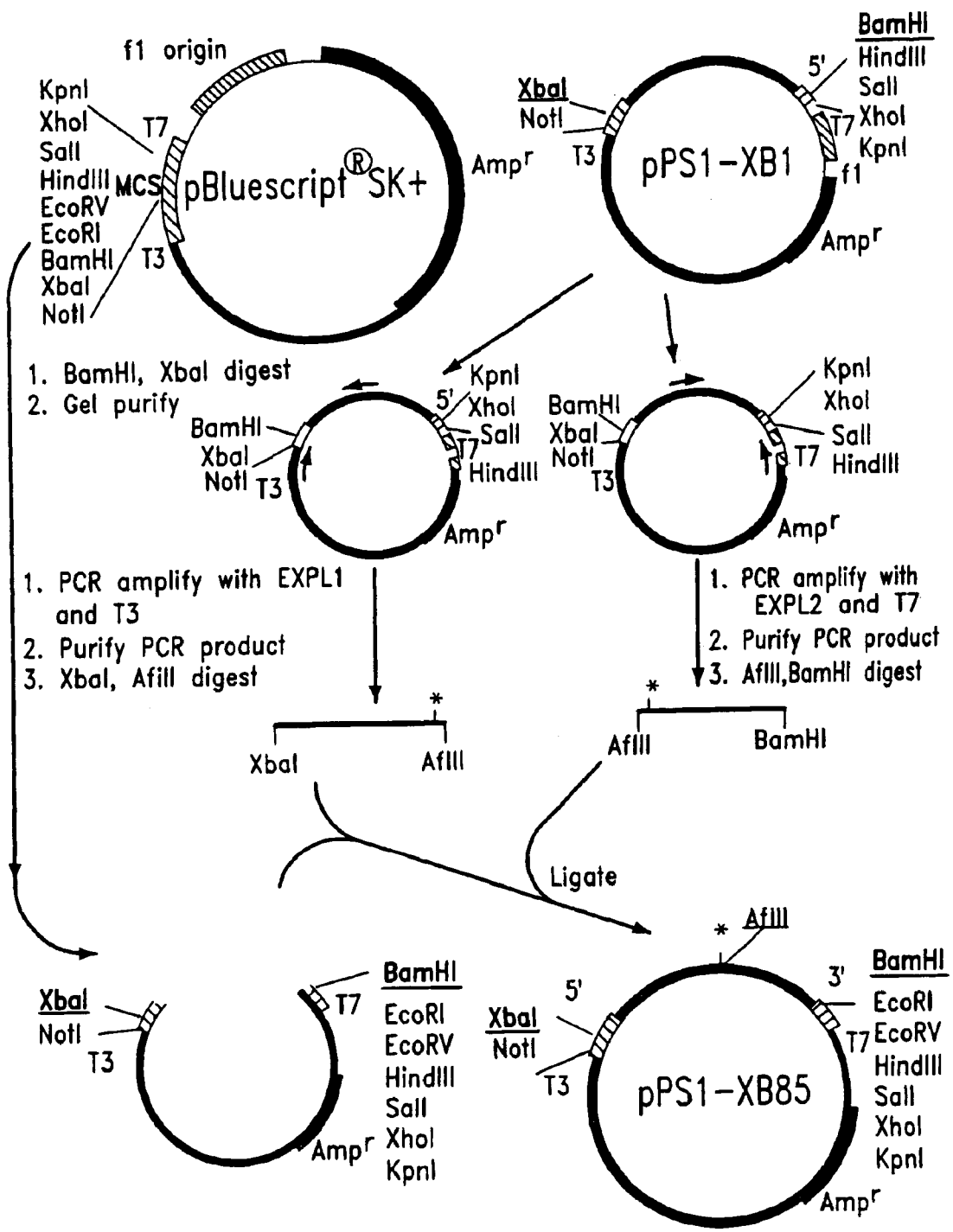
FIG. 14 is a schematic diagram illustrating the construction of plasmid pPS1-XB85.

The second PCR reaction used the primers EXPL1 (CGG ACC CTT AAG ACA CAA AAC AGC CAC; SEQ ID NO:12) and T3 (Stratagene Cloning Systems, La Jolla, Calif.). This generated a 137 bp fragment that encompassed the 5' end of exon 8 and PS1 -XB1. This fragment also included the P264L change and an AflII site (FIG. 14).

The product of the first reaction was purified using Magic™ PCR Preps DNA Purification System (Promega Corporation, Madison, Wis.) and digested with BamHI and AflII in order to liberate the restriction sites at its ends. Similarly, the product of the second reaction was purified and digested with AflII and XbaI. These two fragments, as well as XbaI and BamHI digested pBlueScript® SK+ were ligated together and transformed into HB101 competent *E. coli* cells. The DNA was isolated and analyzed from the ampicillin resistant colonics. The clone bearing a recombinant plasmid in which the two PCR fragments had joined together at their AflII site and inserted into the BamHI and XbaI sites of pBlueScript® SK+ was called pPS1-XB85 (FIG. 14). To confirm the sequences of the mutagenized exon 8, direct nucleotide sequencing (Sanger, *Proc. Natl. Acad Sci. USA*, 1977, 74, 5463–5467) was performed using T3 and T7 sequencing primers (Stratagene Inc., La Jolla, Calif.) and Sequenase Version 2.0 DNA Sequencing Kit (United States Biochemical, Cleveland, Ohio).

Figure 15:
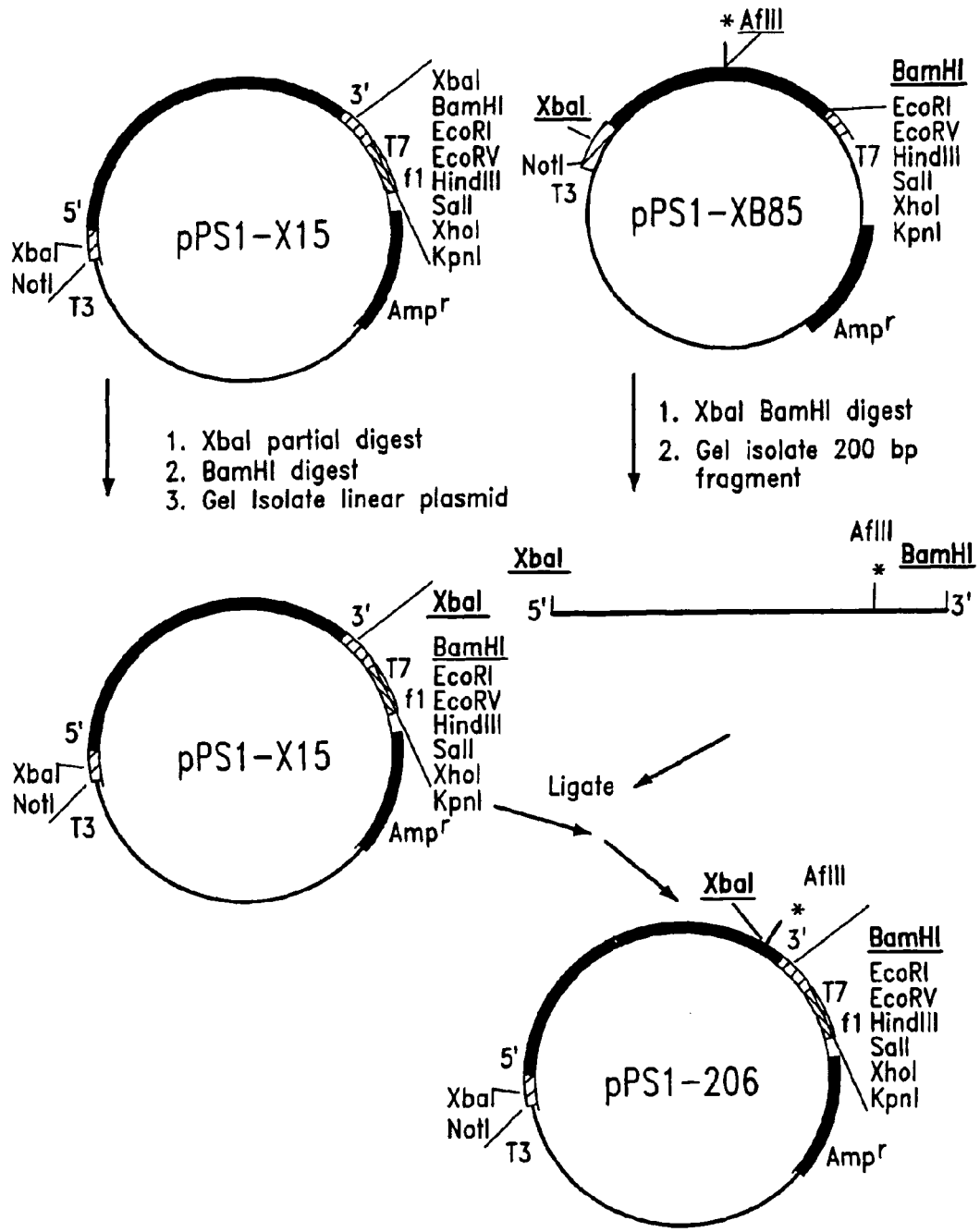
FIG. 15 is a schematic diagram illustrating the construction of plasmid pPS1-206.

The 5' arm of homology was assembled in pBlueScript® SK+ through several cloning steps. First, pPS1-XB15 was partially digested with XbaI so that only one XbaI site was cut. The resulting DNA was then digested with BamHI and gel purified (FIG. 15).

The mutated insert in pPS1-XB85 was released by digesting it with XbaI and BamHI and gel purifying the resulting mutated insert. The 200 bp XbaI-BamHI fragment was ligated into the linearized pPS1-X15 and recombinant plasmids were screened for the proper orientation of the insert by means of an AflII digest. The correctly oriented plasmid yielded 1.9 kb and 5.8 kb fragments. This plasmid was designated "pPS1-206."

Figure 16:
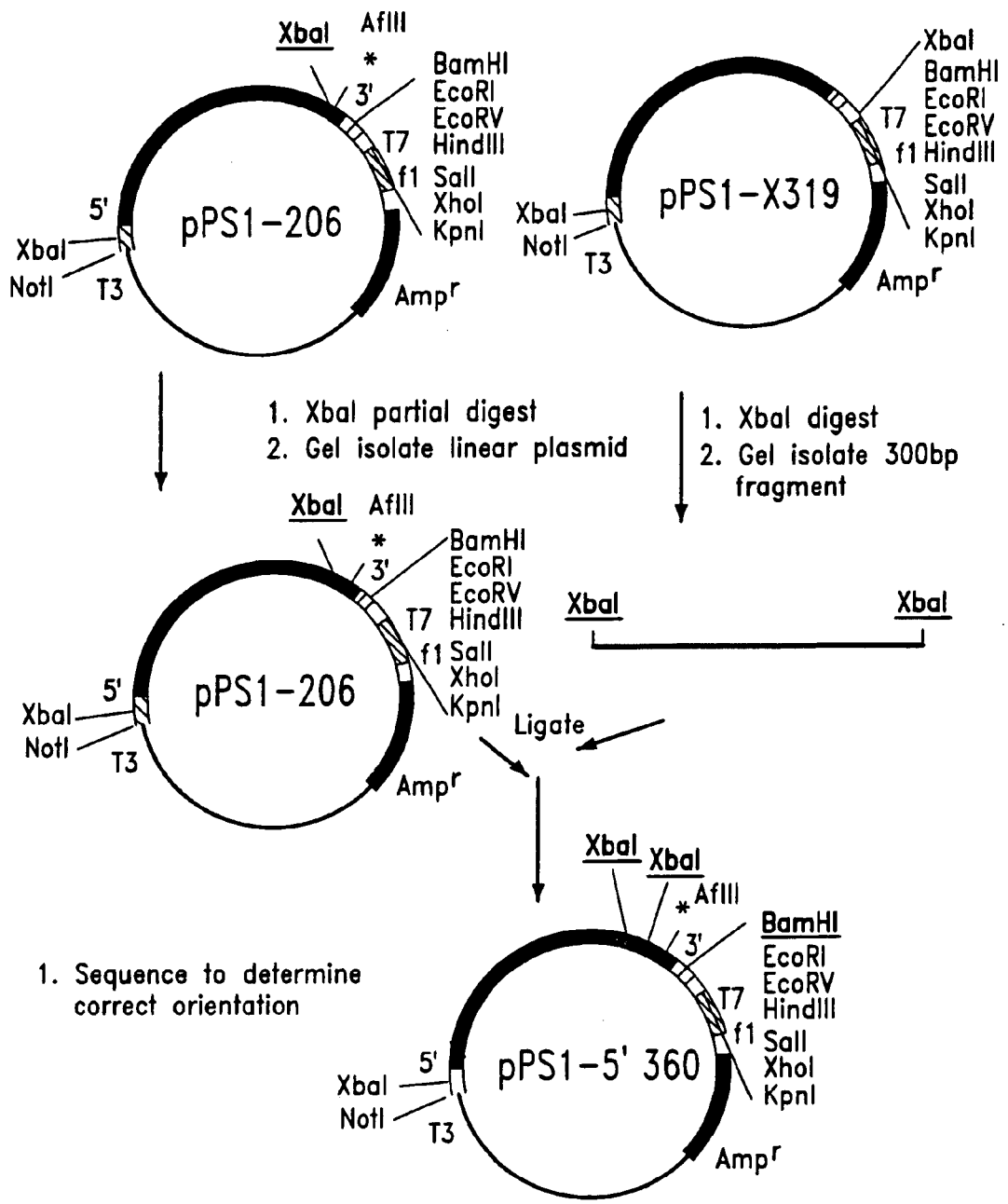
FIG. 16 is a schematic diagram illustrating the construction of plasmid pPS1-360.

To insert the small 300 bp XbaI fragment 5' relative to the mutated 200 bp XbaI-BamHI fragment, pPS1-206 was linearized by a partial XbaI digest (FIG. 16). The XbaI fragment from pPS1-X319 was isolated and cloned into the linearized pPS1-206 DNA. Orientation of the 300 bp XbaI fragment was determined by sequencing the recombinant clone as well as λPS1-20 with primer EX8PL1 using the Thermo Sequenase radiolabeled terminator cycle sequencing kit (Amersham Life Science Inc., Cleveland, Ohio). A plasmid clone that shared sequence identity with λPS1-20 beyond the XbaI site had the 300 bp XbaI fragment inserted in the proper orientation. This plasmid, which contained the assembled 5' arm, was designated "pPS1-5'360" (FIG. 16).

(e) Assembling the Targeting Vector pPS-1-8-TV.

Figure 17:
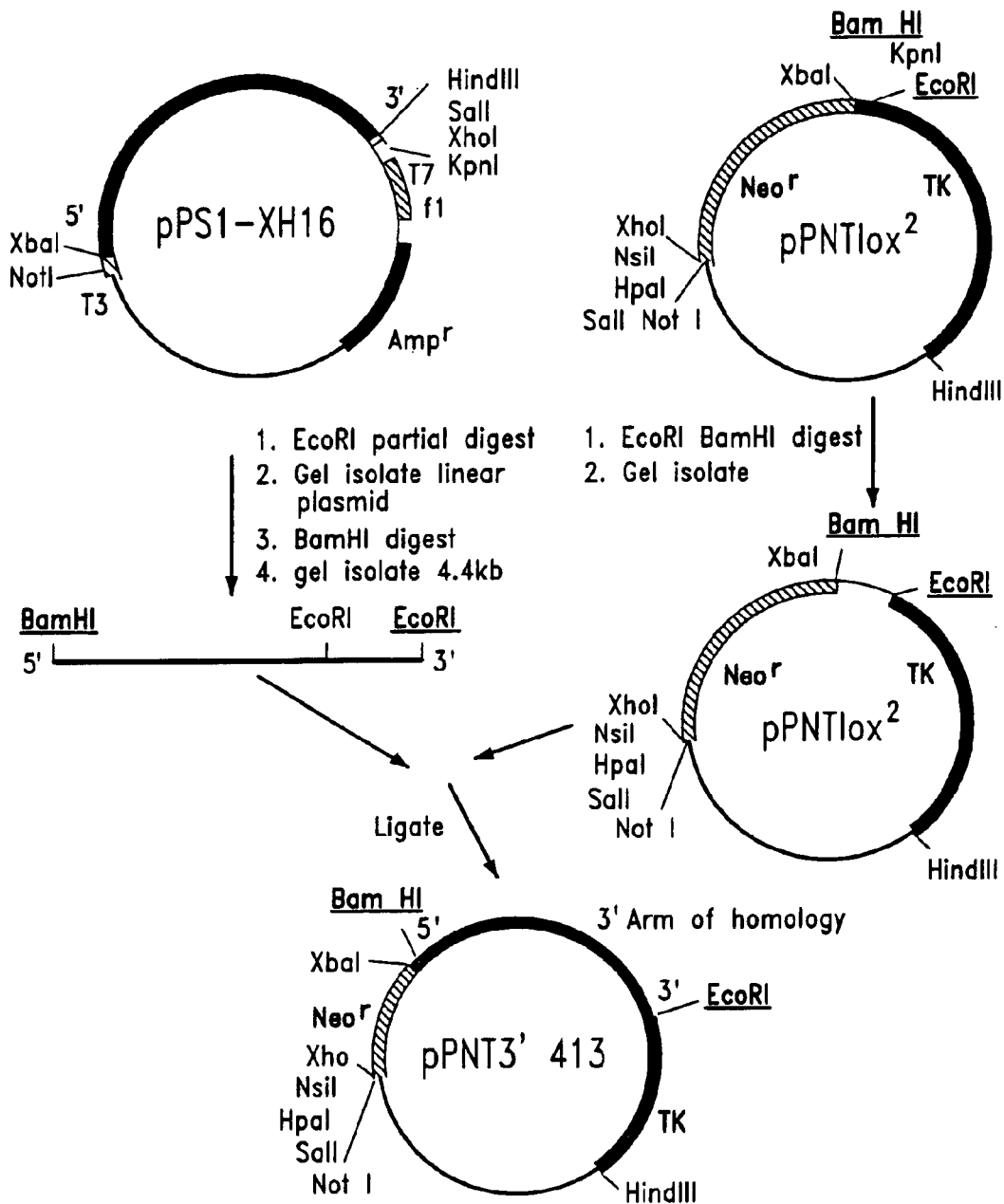
FIG. 17 is a schematic diagram illustrating the construction of plasmid pPNT3'413.

The plasmid pPNTIox$^2$ was prepared for receiving the 3' arm of homology by first digesting plasmid DNA with EcoRI and BamHI and gel isolating the linear plasmid (FIG. 17). In parallel, the 3' arm was prepared by partially digesting pPS1-XH16 with EcoRI and isolating the linear form. This fragment was then digested with BamHI and the 4.1 bp fragment gel isolated. The 3' arm was ligated to pPNTIox$^2$. The resulting plasmid was designated "pPNT3'413."

Figure 18:
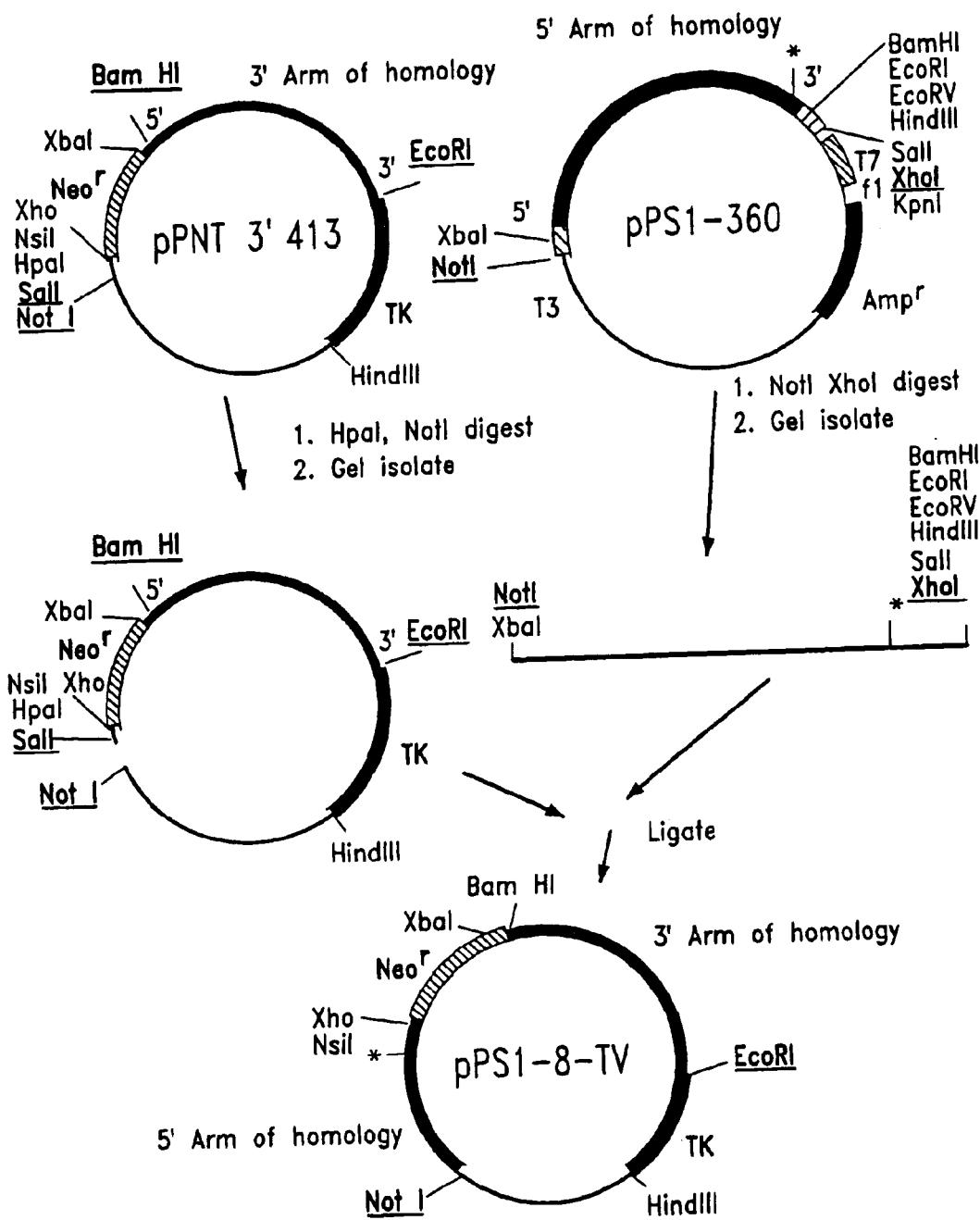
FIG. 18 is a schematic diagram illustrating the construction of plasmid pPS1-8-TV.

The 5' arm was inserted into pPNT3'413 to give the final plasmid pPSI-8-TV. The 5' arm was liberated from plasmid DNA by first digesting with XhoI and NotI. In parallel, pPNT3'413 was prepared by double digesting with NotI and SalI. The two fragments of DNA were ligated and transformed into competent WM 1100 *E. coli* cells (FIG. 18).

Additional vectors can be prepared in the manner described above in order to comprise other human mutations.

Example 3

Mutagenesis of the Mouse PS-1 Gene in ES Cells (a) Cells.

The R1 line of ES cells derived from 129/Sv×129/Sv-CP FI hybrid mice (Nagy et al., *Proc. Natl. Acad. Sci. USA*, 1993, 90, 8424–8429) and obtained from Dr. Janet Rossant (Mt. Sinai Hospital, Toronto, Ontario, Canada) was utilized. These cells were grown in ES cell medium consisting of Dulbecco's Modification of Eagle's Medium (with L-glutamine and 4500 mg/L glucose; Mediatech Inc., Herndon, Va.) supplemented with 20% fetal bovine serum (FBS; Hyclone Laboratories Inc., Logan, Utah; cat. # A-1115; Lot# 11152154), 0.1 mM non-essential amino acids (Mediatech 25-025-L1), 2 mM L-glutamine (Mediatech 25-005-L1), $10^{-6}$ M β-mercaptoethanol (Gibco 21985-023) 1 mM sodium pyruvate (Mediatech 25-000-L1), 1×concentration of a penicillin streptomycin solution (Mediatech 30-001-L1) and 1000 U/ml of leukemia inhibitory factor (Gibco BRL 13275-029). The cells were grown on tissue culture plastic that had been briefly treated with a solution of 0.1% gelatin (Sigma G9391).

The cultures were passed every 48 hours or when the cells became about 80% confluent. For passage, the cells were first washed with phosphate buffered saline (without $Ca^{2+}$ and $Mg^{2+}$) and then treated with a trypsin/EDTA solution (0.05% trypsin, 0.02% EDTA in PBS without $Ca^{2+}$ and $Mg^+$). After all of the cells were in suspension, the trypsin digestion was stopped by the addition of tissue culture medium. The cells were collected by centrifugation, resuspended in 5 ml of tissue culture medium and a 1 ml aliquot of the cell suspension was used to start a new plate of the same size.

(b) DNA Transfection of ES Cells.

pPS1-8-TV DNA (400 µg) was prepared for electroporation by digesting it with NotI in a 1 ml reaction volume. The DNA was then precipitated by the addition of ethanol, washed with 70% ethanol and resuspended in 500 µl of sterile water.

The NotI-linearized pPS1-8-TV DNA was electroporated into ES cells using a Bio-Rad Gene Pulser® System (Bio-Rad Laboratories, Hercules, Calif.). In each of 10 electroporation cuvettes, 40 µg of DNA was electroporated into 2.5×10$^6$ cells suspended in ES cell culture medium. The electroporation conditions were 250 V and 500 µF which typically result in time constants ranging between 6.0–6.1 seconds. After electroporation the cells were incubated for 20 minutes at room temperature in the electroporation cuvettes. All the electroporated cells were then pooled and distributed equally onto 10 gelatinized plates. After 24 hours the plates were aspirated and fresh ES cell medium was added. The next day, the medium in 9 plates was replaced with ES cell medium supplemented with 150 µg/ml of G41 (Gibco) and 0.2 µM gancyclovir (Syntex) while one plate received medium supplemented only with 150 µg/ml of G418. After an additional 8 days, resulting individual ES cell colonies were picked off of the plates and separately expanded in a well of 24-well plates as described by Wurst et al., pp 33–61 in *Gene Targeting* Vol. 126, 1993, Edited by A. L. Joyner, IRL Press, Oxford University Press, Oxford, England. Comparison of the number of colonies that grew on the plates supplemented with G418 and gancyclovir versus the number that grew with only G418 supplementation was used to determine the efficiency of negative selection.

(c) Analyses of the ES Cell Transformants.

When the cell culture in each well of the 24-well plates became approximately 80% confluent, it was washed and the cells were dispersed with two drops of trypsin-EDTA. Trypsinization was stopped by the addition of 1 ml of ES cell medium. An aliquot (0.5 ml) of this suspension was transferred to each of two wells of separate 24-well plates. After the cells had grown to near confluence, one of the plates was used for cryopreservation of the cell line while the other was used as a source of DNA for each of the clones.

For cryopreservation, the cells in a 24-well plate were first chilled by placing the plate on ice. The medium was then replaced with fresh ES cell medium supplemented with 10% DMSO and 25% FBS and the plate was cooled at approximately 0.5° C./min by insulating the plate in a styrofoam box and placing it in a −70° C. freezer.

To isolate the DNA from the clones on the other plate, the medium in each well was replaced with 500 µl of digestion buffer (100 mM Tris-HCl, pH 8.5, 5 mM EDTA, 0.2% SDS, 200 mM NaCl, 100 µg/ml proteinase K). After overnight incubation at 37° C., 500 µl of isopropanol was added to each well and the plate was agitated for 15 minutes on an orbital shaker. The supernatant was aspirated and replaced with 500 µl of 70% ethanol and the plate was shaken for an additional 15 minutes. The DNA precipitate was picked out of the well and dissolved in 50 µl of TE solution (10 mM Tris-HCl pH 7.5, 1 mM EDTA).

The primary analysis for mutagenesis of the mouse PS-1 gene involved a Southern hybridization screen of ApaI digested ES cell DNA. The probe for this analysis was derived from the 3' end of our cloned PS-1 region outside of the 3' arm of homology (FIG. 19d). It was prepared by first isolating the 6 kb XbaI fragment corresponding to the 3' end of λPS1-6 (FIG. 2) and subcloning it into XbaI digested pBlueScript® SK+. A further digest of this subclone, called pPS1-X6 with XhoI (an internal site) and HindIII (from the Bluescript® S K+ polylinker) yielded the 1000 bp probe.

Figure 19:
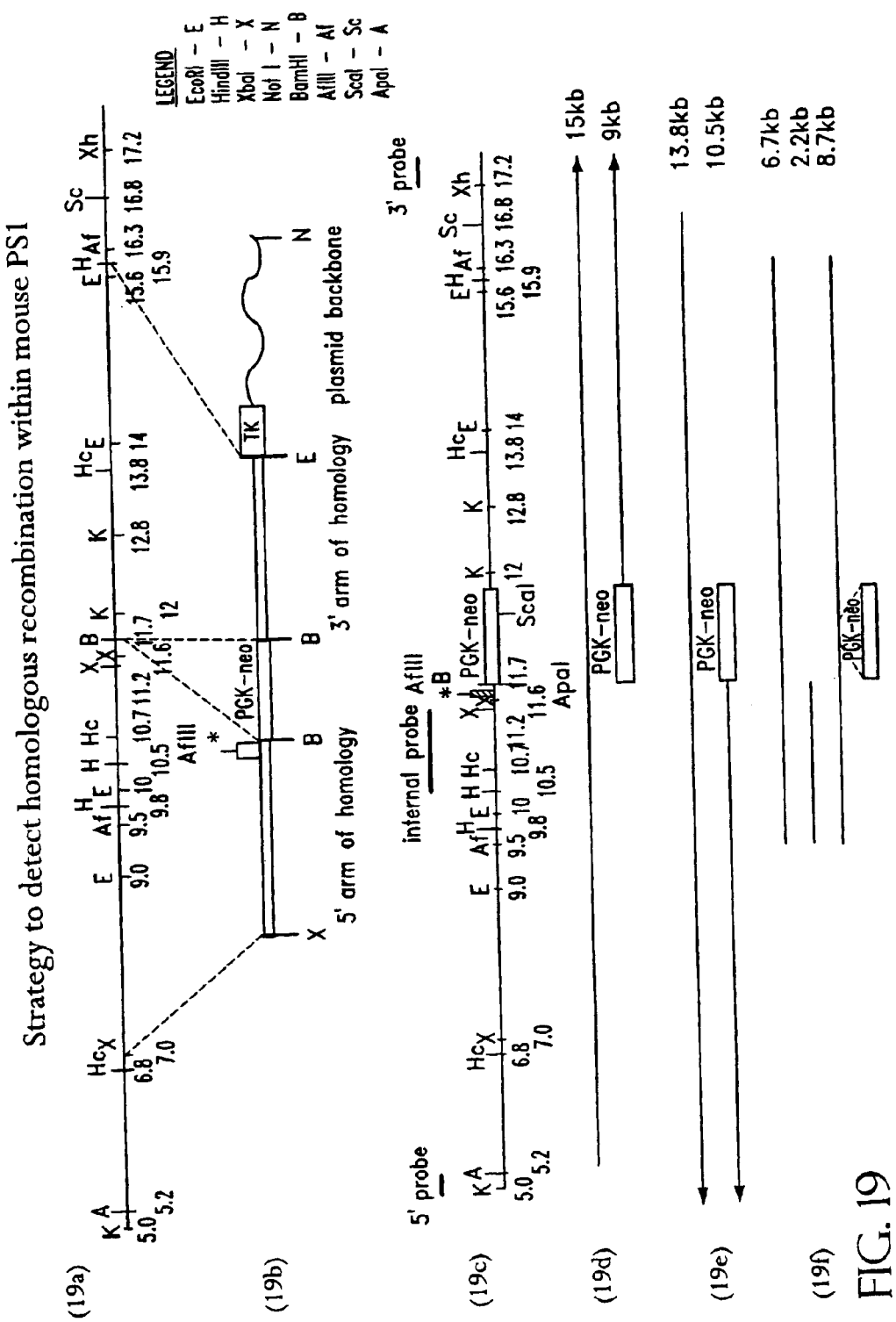
FIG. 19 is a schematic diagram illustrating the strategy to detect homologous recombination within mouse PS1. Letter abbreviations for restriction endonucleases are as follows: E, EcoRI; X, XbaI; N NotI; H, HindIII; B, BamHI; A, ApaI; Af, AflII; Sc, ScaI; K, KpnI; and Hc, HincII.

For the Southern hybridization screen, an aliquot (10 µl) of each ES cell clone DNA was digested with ApaI, resolved on a 0.8% agarose gel, and transferred to a GeneScreen Plus® membrane. The probe was labelled with $^{32}$P-dCTP by random priming and hybridized overnight to the membrane at 58° C. (Church et al., *Proc. Natl. Acad Sci, USA*, 1984, 81, 1991–1995). An ES cell line in which the PS-1 gene has successfully undergone homologous recombination yields 9 and 15 kb ApaI fragments in this assay (FIG. 19). This is because homologous recombination advantageously introduces a novel ApaI site into the region where the neo$^r$ cassette is incorporated. The 15 kb band represents the unaltered cellular copy of PS-1 while the 9 kb band is derived from the PS-1 copy in which the novel ApaI site results in a shorter fragment. In this first screen, 8 cell lines were identified as potential targeted cell lines out of 260 cell lines analyzed.

All cell lines scored as putative homologous recombinants by the primary screen were then further screened using a 500 bp KpnI-ApaI fragment isolated from a 5.5 kb 5' XbaI fragment from λPS1-20 on ScaI digested ES cell DNA. In this case, the normal PS-1 gene yielded a 13.8 kb fragment and the mutant PS-1 gene a 10.5 kb fragment (FIG. 19e). Of the 8 cell lines examined in this screen, 4 were shown to have undergone homologous recombination at their 5' end.

Cell lines that were identified as having undergone homologous recombination by both screens were considered to have undergone bona fide homologous recombination (as opposed to homologous insertion which would give positive results for only 1 of the 2 preceding screens). However, depending on where crossover takes place when the 5' arm recombines, the mutations that were included in this arm may or may not have been incorporated into cellular DNA as a result of proper homologous recombination (FIG. 1). A further Southern hybridization screen aimed at detecting the novel AflII site created as a result of the P264L mutation was therefore implemented. For this, a 1.2 kb HindIII-XbaI fragment isolated from pPS1-X15 as a probe on AflII digested DNA was utilized. An unaltered PS-1 gene yielded a 6.7 kb band (FIG. 19f). A PS-1 gene in which proper homologous recombination has taken place, but which lacks the planned mutations yields a 8.7 kb band while the inclusion of the planned mutations yields a 2.2 kb band. Of the 4 bona fide homologous recombinant cell lines examined, all 4 were shown to have incorporated the novel AflII site near the planned mutations.

The mutagenized form of the PS-1 gene described here has been called PS1$^{nP264L}$ as opposed to the normal PS-1 gene termed PSI$^+$. The four ES cell lines bearing one copy of PS1$^{nP264L}$ have been called, PS1-87, PS1-175, PS1-176, and PS1-243. Three of these lines were thawed, cell numbers expanded, and used to establish PS-1 mutant mice.

Additional mutagenesis of the mouse PS-1 gene can be performed in ES cells in the manner described above in order to comprise other human mutations.

Example 4

Establishment of PS-1 Mutant Mice

PS-1 mutant ES cells were used to make chimeric mice by aggregating the mutant ES cells to E2.5 embryos and transferring the aggregated embryos to pseudopregnant females (Wood et al., *Nature*, 1993, 365, 87–89). ES cells were prepared for aggregation by limited trypsinization to produce clumps that average 10–15 cells. E2.5 embryos were collected from superovulated CD-1 female mice by oviduct flushing as described by Hogan et al., *Manipulating the Mouse Embryo: A Laboratory Manual*, 1986, Cold Spring Harbor Laboratory, Cold Spring Harbor, New York). The zona pelucida was removed from the embryos using acidic Tyrode's solution (Sigma Chemical Co., St. Louis, Mo.). Aggregation wells were created by pressing a blunt metal instrument (a darning needle) into tissue culture plastic. Embryos were then placed in a well together with a clump of approximately 10–15 ES cells in a small drop (approximately 20 µl) of M16 medium (Sigma Chemical Co., St. Louis, Mo.) under mineral oil. After an overnight incubation (37° C., 100% humidity, 5% $CO_2$ in air) the aggregate embryos were transferred to the uterine horns of a pseudopregnant female (Hogan et al., 1986, supra). Contribution of the ES cells to the offspring was scored by the appearance of pigmented coat color. Positive mice are termed chimeric founders. Germline contribution by the ES cells was scored by the appearance of pigmented offspring from a cross between the chimeric founders and CD-1 females.

Example 5

Chimeras

Of 3 mutant PS-1 ES cell lines used in embryo aggregations, one produced a germline chimera:

TABLE 1

| Clone | Number of Embryo Aggregation | Number of Chimeric Founders | Number of Germline Chimeras |
| --- | --- | --- | --- |
| PSI-175 | 400 | 5 | 1 |
| PSI-176 | 75 | 4 | 0 |
| PSI-243 | 120 | 0 | 0 |

The germline chimera was then used to establish lines of mice carrying PS-1$^{nP264L}$. The presence of the mutant PS-1 allele in the pigmented offspring was determined using a PCR strategy aimed at detecting the neo$^r$ cassette, following substantially the same procedure as set forth in Example 1. PCR primers were as follows: neo28 (GGA TTG CAC GCA GGT TCT CC; SEQ ID NO:13); and neo445 (CCG GCT TCC ATC CGA GTA CG; SEQ ID NO:14). The genomic DNA was prepared from a tail sample (Hogan, 1986, supra). Of the four pigmented offspring, one female mouse was heterozygous for PS-1$_{nP264L}$ (PS-1$^{nP264L/+}$), i.e., this mouse was positive for the neo$^r$ cassette based upon the foregoing PCR strategy. Subsequent generational offspring which are also heterozygous for PS-1$^{nP264L}$ have been developed by mating of this female with wild-type males.

Mice heterozygous for PS-1$_{nP264L}$ (PS-1$^{nP264L/+}$) were genotyped using a PCR-based method. The presence of the wild-type allele for murine PS-1 was scored using the following primers: X8F (CCC GTG GAG GAG GTC AGA AGT CAG; SEQ ID NO:15) and X8R (TTA CGG GTT GAG CCA TGA ATG; SEQ ID NO:16). Scoring with these primers yields a 142 bp fragment (data not shown). The presence of the mutant allele was scored using the primers neo28 and neo445, which yields a 417 bp fragment. Thus, mice which are heterozygous for the mutation yield both bands; mice which are homozygous for the mutation yield only the 417 bp band; and mice that are homozygous for the wild-type allele yield only the 142 bp band. Tissue samples were derived from animal tails, and the PCR procedures of Example 1 were utilized for such scoring.

Mice homozygous for the PS-1$^{nP264L}$ allele (i.e., PS-1$^{nP264L/nP264L}$) were generated by cross breeding of heterozygous mice (PS-1$^{nP264L/+}$) with mice which are homozygous for a humanized APP gene (as disclosed in PCT Publication Number WO96/34097, published Oct. 31, 1996; incorporated herein fully by reference). The resulting generational offspring were then determined to be heterozygous for both the PS-1$^{nP264L}$ allele and heterozygous for the humanized APP gene (data not shown); these generational offspring were then utilized for cross-breeding, with resulting generational offspring determined (using the PCR procedure outlined above) to be homozygous for the PS-1$^{nP264L}$ allele, as well heterozygous for the humanized APP gene (generational offspring from this liter were also found to be heterozygous for the PS-1$^{nP264L}$ allele/homozygous for the humanized APP gene; and heterozygous for the PS-1$^{nP264L}$ allele/heterozygous for the humanized APP gene—due to the limited number of pups obtained from this liter, double homozygotes were not found). Subsequent matings produced PS-1$^{nP264L/nP264L}$×APP$^{NLh/NLh}$ mice.

Mice homozygous for the PS-1$^{nP264L}$ allele were also generated by cross-breeding of heterozygous mice (PS-1$^{nP264L/+}$). In one set of matings, 6 homozygotes were found amongst 27 offspring, which is well within the expected 25% recovery of homozygotes from a heterozygous cross.

Accordingly, and based upon the various breeding approaches disclosed above, substantially normal viability and embryonic survival of the animals is evident.

Example 6

Excision of the PGK-Neo Cassette pBS185 plasmid DNA (Sauer et al., New Biol., 1990, 2, 441–449, incorporated herein by reference in its entirety) encoding Cre recombinase was introduced by pronuclear injection into one-cell embryos generated from a PS-1$^{nP264L/+}$×CD-1 cross. Since the plasmid was circular, DNA integration into the genome had a very low frequency of occurrence. Transient expression of the DNA to produce Cre recombinase excised the PGK-neo cassette in the early embryos. Injected embryos were transferred to pseudopregnant females. Excision of the PGK-neo cassette was confirmed by genotyping of the offspring. These mice were designated PS-1$^{P264L/+}$ and were crossed to generate PS-1$^{P264L/P264L}$ mice.

Because the neomycin-selectable marker reduced transcription of the PS-1 gene, the PGK-neo gene was excised by recombination at the flanking loxP sites after transient expression of Cre recombinase. One-cell embryos (n=154) generated by a PS-1$^{nP264L/+}$×CD-1 cross were injected with pBS185 plasmid DNA and implanted into pseudopregnant females. The loss of the PGK-neo gene was scored in the offspring as a 219-base pair fragment by PCR using the X8F and X8R primer pairs as described in Example 5. The mutant PS-1 allele with the neomycin-selectable marker excised was designated PS-1$^{P264L}$. Successful excision occurred in one founder mouse that generated heterozygous (PS-1$^{P264L/+}$) and homozygous (PS-1$^{264L/P264L}$) lines of mice. PS-1$^{P264L/+}$ mice were crossed with Tg2576 mice and APP$^{NLh/NLh}$ mice to further study the effects of the P264L mutation on Aβ production and deposition.

Example 7

Northern And Western Blots

PS-1$^{+/+}$, PS-1$^{nP264L/nP264L}$, and PS-1$^{P264L/P264L}$ mice, aged 2–6 months were used for evaluating mRNA and protein levels of PS-1. Total RNA was extracted from one-half brain by homogenization in RNAzol B (Tel-Test, Friendswood, Tex.). Messenger RNA was selected with Oligotex columns (Qiagen, Valencia, Calif.). Equal volumes of mRNA were mixed with loading buffer (NorthernMAX-Gly, Ambion, Austin, Tex.) heated to 50° C. for 30 min, separated on a 0.7% agarose gel, and transferred to a nylon membrane. PS-1 mRNA was detected with a $^{32}$P-dUTP-labeled riboprobe representing the 3' end of human PS-1: nucleotides 1083–1428 cloned into a pGEM-T vector (Promega, Madison, Wis.). The same blot was hybridized with a GAPDH probe (Ambion) for normalization. To visualize mRNAs, the membrane was exposed to a phosphor screen, scanned on a Storm 840 PhosphorImager, and densitometry performed with ImageQuaNT software (Molecular Dynamics, Sunnyvale, Calif.).

One-half brain was homogenized in 2.5 ml of buffer containing 10 mM Tris pH 7.4, 150 mM NaCl, 5 mM EDTA, 1% SDS, 0.25% deoxycholate, 0.25% NP-40, and protease inhibitors (5 mM PMSF, 10 µg/ml aprotinin, 10 µg/ml leupeptin, 10 µg/ml pepstatin) (Lee et al., Nature Med., 1997, 3, 756–760). Protein concentration was determined by BCA assay (Pierce, Rockford, Ill.). Total brain lysates were mixed with reducing loading buffer and heated at 37° C. for 45 min. Fifty µg total protein of each sample was separated by electrophoresis on NuPAGE 10% polyacrylamide gels (Novex, San Diego, Calif.), and transferred to nitrocellulose. Membranes were blocked overnight at 4° C. in Tris buffered saline (TBS) with 0.05% Tween-20, and 5% nonfat dry milk. PS-1 was detected with rabbit polyclonal antibodies diluted in the same solution. The C-terminal fragment was detected with antibody B17.2 (De Strooper et al., J. Biol. Chem., 1997, 272, 3590–3598) at 1:2000 dilution. B17.2 was raised against amino acid residues 300–315 (EGDPEAQRRVSKNSKY; SEQ ID NO:17) in the hydrophilic loop domain of human PS-1. The N-terminal fragment was detected with CP160 at 1:500. CP160 was generated using a 6X-histidine tagged N-terminal fragment of human PS-1 (amino acids 1–80), expressed in bacteria with a pQE-9 plasmid (Qiagen). The synthetic PS-1 N-terminal fragment was purified using Ni-NTA agarose (Qiagen) and SDS-PAGE. Peptide was cut out of acrylamide gels for injection into rabbits. The IgG fraction of CP 160 was affinity purified and used for blotting. The primary antibodies were detected with horseradish peroxidase-conjugated anti-rabbit secondary antibodies (New England Biolabs, Beverly, Mass.). Blots were reacted with chemiluminescent reagent (LumiGLO, New England Biolabs) and exposed to Hyperfilm (Amersham, Arlington Heights, Ill.). Films were scanned and densitometry performed with RFLP2.1 software (Scanalytics, Fairfax, Va.).

Northern blot analysis demonstrated a 3.1 kb band for PS-1 mRNA. PS-1 mRNA levels were normalized for loading differences with GAPDH mRNA levels. The presence of the PGK-neo gene in the PS-1$^{nP264L/nP264L}$ mice resulted in levels of PS-1 mRNA that were 20% of wild type levels (data not shown). mRNA levels in PS-1$^{P264L/P264L}$ mice were 100% of PS-1$^{+/+}$ mice (data not shown). Thus, removal of the PGK-neo cassette returned PS-1 mRNA levels to normal levels.

Western blotting demonstrated an N-terminal PS-1 fragment of ~30 kDa using antibody CP160 and a C-terminal PS-1 fragment of ~20 kDa using antibody B17.2 in all three genotypes. Blotting with CP 160, preabsorbed with antigen, eliminated the ~30 kDa N-terminal band (data not shown). Specificity of B 17.2 for the C-terminal PS-1 fragment has been previously demonstrated (De Strooper et al., *J. Biol. Chem.*, 1997, 272, 3590–3598). Because PS-1 mRNA levels were reduced in the PS-1$^{nP264L/nP264L}$ mice, the level of PS-1 protein was also reduced to approximately 15–20% of normal levels (data not shown). In spite of normal mRNA expression of mutant PS-1 in the PS-1$^{P264L/P264L}$ mice, PS-1 protein levels were reduced by about 50% (data not shown). Both the N- and C-terminal fragments were reduced to a similar degree. These data indicate that the PS-1$^{P264L}$ mutation affects PS-1 protein levels either via effects on translation, processing of the full length PS-1 protein, or stability of the cleaved fragments. Reports have described variable reductions in the N-terminal fragment and/or accumulation of holoprotein due to some FAD mutations in PS-1 (Mercken et al., *FEBS Lett.*, 1996, 389, 297–303; Murayama et al., *Neurosci. Lett.*, 1997, 229, 61–64; Levey et al., *Ann. Neurol.*, 1997, 41, 742–753; Murayama et al., *Prog. Neuro-Psychopharmacol. Biol. Psychiatr.*, 1999, 23, 905–913; Takahashi et al., *Neurosci. Lett.*, 1999, 260, 121–124). In contrast, a variety of PS-1 FAD mutations were found to cause no reductions in fragment formation in FAD patients, in transfected cells, and in transgenic or gene-targeted mice (Hendriks et al., *NeuroReport*, 1997, 8, 1717–1721; Lee, et al., *Nature Med.*, 1997, 3, 756–760; Podlisny et al., *Neurobiol. Dis.*, 1997, 3, 325–337; Guo et al., *Nature Med.*, 1999, 5, 101–106; Lévesque et al., *Molec. Med.*, 1999, 5, 542–554; Vanderhoeven et al., *Neurosci. Lett.*, 1999, 274, 183–186; Borchelt et al., *Neuron*, 1996, 17, 1005–1013; Duff et al., *Nature*, 1996, 383, 710–713; Citron et al., *Nature Med.*, 1997, 3, 67–72; Nakano et al., *Eur. J. Neurosci.*, 1999, 11, 2577–2581). The level of reduction in the N-terminal fragment for the P264L mutation was to about 35–40% of wild type PS-1 values in transfected PC12 cells (Murayania et al., *Prog. Neuro-Psychopharmacol. Biol. Psychiatr.*, 1999, 23, 905–913), consistent with the degree of reduction that has been seen in the PS-1$^{P264L/P264L}$ mice compared with PS-1$^{+/+}$ mice.

Example 8

Aβ40- and 42-Specific ELISAs

Half brains from predepositing double gene-targeted mice (APP$^{NLh/NLh}$ mice at 1–6 months, APP$^{NLh/NLh}$×PS-1$^{P264L/+}$ mice at 5 months, and APP$^{NLh/NLh}$×PS-1$^{P264L/P264L}$ mice at 1–2 months) and predepositing Tg2576 mice (Hsiao et al., *Science*, 1996, 274, 99–102) at 2–4 months were frozen on dry ice and stored at −70° C. Additional half brains from predepositing Tg2576 mice crossed with PS-1$^{P264L/+}$ mice (Tg2576×PS-1$^{+/+}$ mice at 2–4 months, Tg2576×PS-1$^{P264L/+}$ mice at 2 months, a Tg2576×PS-1$^{P264L/P264L}$ mice at 1 month) were similarly prepared. Half brains were homogenized in 4 ml of 0.2% diethylamine and 50 mM NaCl and centrifuged at 100,000×g. The supernatants were neutralized to pH 8 with 2 M Tris-HCl, assayed for protein concentration by the BCA method (Pierce, Rockford, Ill.), and diluted 1:1 in 5% fetal clone serum (HyClone, Logan, Utah) and 1% nonfat dry milk in TBS. The Aβ42-specific ELISA was run as previously described (Savage et al., *J. Neurosci.*, 1998, 18, 1743–1752). The Aβ40-specific ELISA was modified (Savage et al., *J. Neurosci.*, 1998, 18, 1743–1752) so that the capture antibody was 6E10 (Senetek, Napa, Calif.) and the detecting antibody was selective for Aβ40 (BioSource International, Camarillo, Calif.). ELISA signals were reported as nanograms of Aβ per milligram of total extracted protein based upon standard curves generated using Aβ40 or 42 (Bachem, King of Prussia, Pa.).

Table 2 shows the effect of the PS-1$^{P264L}$ mutation on Aβ40 and Aβ42 levels in the brains of APP$^{NLh/NLh}$ mice before the appearance of Aβ deposition. The PS-1$^{P264L}$ mutation did not have a significant effect on the level of Aβ40. One copy of the PS-1$^{P264L}$ mutation slightly elevated Aβ42 but the effect of the mutation was significant only in the APP$^{NLh/NLh}$×PS-1$^{P264L/P264L}$ mice compared with the APP$^{NLh/NLh}$×PS-1$^{+/+}$ mice. This increase in Aβ42 levels caused a significant elevation in the ratio of Aβ42 to Aβ40 in the APP$^{NLh/NLh}$×PS-1$^{P264L/P264L}$ mice relative to APP$^{NLh/NLh}$×PS-1$^{+/+}$ and APP$^{NLh/NLh}$×PS-1$^{P264L/+}$ mice. Tg2576 mice had markedly more Aβ40 and Aβ42 than the APP$^{NLh/NLh}$×PS-1$^{P264L/P264L}$ mice but the ratio of Aβ42/40 was similar in the Tg2576 and APP$^{NLh/NLh}$×PS-1$^{+/+}$ mice.

Table 3 shows the effect of the PS-1$^{P264L}$ mutation on Aβ40 and Aβ42 levels in the brains of Tg2576 mice before the appearance of Aβ deposition. The PS-1$^{P264L}$ mutation did not have a significant effect on the level of Aβ40. One copy of the PS-1$^{P264L}$ mutation slightly elevated Aβ42 but the effect of the mutation was significant only in the Tg2576×PS-1$^{P264L/P264L}$ mice compared with the Tg2576×PS-1$^{+/+}$ mice. The increase in Aβ42 levels caused a significant elevation in the ratio of Aβ42 to Aβ40 in the Tg2576×PS-1$^{P264L/P264L}$ mice relative to Tg2576×PS-1$^{+/+}$ mice. Thus, the effect of the PS-1$^{P264L}$ mutation on Aβ levels was similar for the Tg2576 and APP$^{NLh/NLh}$ mice.

TABLE 2

Aβ40 and 42 Levels in Predepositing APP$^{NLh/NLh}$ with PS-1$^{P264L}$ Mutations and Tg2576 Mice

| PS-1 Genotype | Age (days) | N | Aβ40 (ng/mg protein) | Aβ42 (ng/mg protein) | Aβ42/20 Ratio |
|---|---|---|---|---|---|
| APP$^{NLh/NLh}$ Mice with PS-1$^{P264L}$ Mutations | | | | | |
| XPS-1$^{+/+}$ | 103 | 8 | 0.40 ± 0.03 | 0.08 ± 0.01 | 0.18 ± 0.03 |
| XPS-1$^{P264L/+}$ | 138 | 5 | 0.47 ± 0.08 | 0.11 ± 0.03 | 0.22 ± 0.02 |
| XPS-1$^{P264L/P264L}$ | 54 | 10 | 0.40 ± 0.03 | 0.15 ± 0.01* | 0.37 ± 0.01** |
| Tg2576 Mice on C57B6/SJL Background | | | | | |
| | 99 | 6 | 1.52 ± 0.17 | 0.29 ± 0.05 | 0.18 ± 0.01 |

± standard error of the mean
*Kruskal-Wallis ANOVA, p = 0.012, PS-1$^{P264L/P264L}$ versus PS-1$^{+/+}$
**ANOVA, p = 1.64 E-8, PS-1$^{P264L/P264L}$ versus PS-1$^{+/+}$, PS-1$^{P264L/+}$, and Tg2576

TABLE 3

Aβ40 and 42 Levels in Predepositing Tg2576 Mice with PS-1$^{P264L}$ Mutations
Tg2576 Mice with PS-1$^{P264L}$ Mutations

| PS-1 Genotype | Age (days) | N | Aβ40 (ng/mg protein) | Aβ42 (ng/mg protein) | Aβ42/40 Ratio |
|---|---|---|---|---|---|
| XPS-1$^{+/+}$ | 92 | 6 | 1.73 ± 0.10 | 0.27 ± 0.2 | 0.16 ± 0.01 |
| XPS-1$^{P264L/+}$ | 62 | 5 | 2.15 ± 0.19 | 0.44 ± 0.07 | 0.20 ± 0.02 |
| XPS-1$^{P264L/P264L}$ | 31 | 8 | 1.72 ± 0.22 | 0.57 ± 0.08* | 0.33 ± 0.01** |

± standard error of the mean
*Kruskal-Wallis ANOVA, p = 0.0024, PS-1$^{P264L/P264L}$ versus PS-1$^{+/+}$
**Kruskal-Wallis ANOVA, p = 5.87 E-4, PS-1$^{P264L/P264}$ versus PS-1$^{+/+}$

Example 9

Immunohistochemistry and Histology

PS-1$^{P264L/P264L}$ mice were examined at 12 months of age. APP$^{NLh/NLh}$ mice that were PS-1$^{+/+}$, PS-1$^{P264L/+}$, or PS-1$^{P264L/P264L}$, aged 3, 6, 9, 12, 15, and 18 months of age were evaluated. Additional mice examined were Tg2576 and were PS-1$^{+/-}$, PS-1$^{264L/+}$, or PS-1$^{P264L/P264L}$, aged 1, 2, 4, 6, 9, 12, 15, and 18 months of age. Other Tg2576 mice maintained by crossing to C57B6/SJL mice were also examined at 6, 9, 12, 15, 18, and 21 months of age. Mice were perfused with Ringer's solution and the brains removed and hemisected. One-half of each brain was immersed in 70% ethanol and 150 mM NaCl for 48 hours, paraffin embedded and sectioned in the sagittal plane at 10 μm. Sets of 16 sections taken at intervals of 200 μm were stained to demonstrate Aβ deposits by immunohistochemistry. Antibodies used were 1153, a rabbit polyclonal antibody generated against amino acids 1–28 of human Aβ (Savage et al., *Neuroscience*, 1994, 60, 607–619) and monoclonal antibodies 4G8 and 6E10 (Senetek). Sections were pretreated with 80% formic acid for 4G8, not pretreated for 1153 and 6E10, and were reacted with the primary antibodies overnight at 1:1,000. Antibodies were complexed using biotinylated secondary antibodies (1:100), linked using streptavidin labeled horseradish peroxidase (BioGenex, San Ramon, Calif.), and visualized using nickel-intensified 3,3'-diaminobenzidene. Non-transgenic mice, as well as pre-absorbed primary antisera, served as staining controls. Additional sets of sections were stained using thioflavine S and examined with a fluorescence microscope.

Plaque load was quantified in neocortex in one set of 16 sections stained with antibody 1153 using the CastGrid system (Olympus, Copenhagen, Denmark). Volume of neocortex and percent volume of neocortex occupied by Aβ deposits were determined stereologically by point counting (Weibel et al., (1979) Stereological methods, vol. 1: practical methods for biological morphometry, 415 pp. London: Academic Press). Representative results are shown in Table 4.

TABLE 4

Aβ Plaque Load (% Volume Fraction) in Neocortex at 6 Months of Age

| Genotype | % Plaque Load |
| --- | --- |
| Tg2576 (C57B6/SJL) | 0.0018 |
| Tg2576 × PS-1$^{+/+}$ | 0.0016 |
| Tg2576 × PS-1$^{P264L/+}$ | 2.92 |
| Tg2576 × PS-1$^{P264L/P264L}$ | 9.09 |
| APP$^{NLh/NLh}$ × PS-1$^{+/+}$ | 0 |
| APP$^{NLh/NLh}$ × PS-1$^{P264L/+}$ | 0 |
| APP$^{NLh/NLh}$ × PS-1$^{P264L/P264L}$ | 0.026 |

Extracellular Aβ deposition was markedly accelerated in Tg2576 mice that were PS-1$^{P264L/+}$ or PS-1$^{P264L/P264L}$ compared with those that were PS-1$^{+/+}$. In Tg2576×PS-1$^{P264L/+}$ mice, Aβ deposition was not noted at 2 months of age but was present at 4 months of age. In Tg2576×PS-1$^{P264L/P264L}$ mice, Aβ deposition was not present at 1 month of age but was present at 2 months of age. Tg2576×PS-1$^{++}$ mice did not show Aβ deposition until 6 months of age, and the amount was comparable to that seen in 6-month-old Tg2576 mice maintained on the C57B6/SJL background. Aβ plaque load visualized with antibody 1153 increased dramatically in neocortex of the Tg2576×PS-1$^{P264L/+}$ and Tg2576×PS-1$^{P264L/P264L}$ mice at later ages (data not shown). Tg2576×PS-1$^{P264L/+}$ mice at 4 months and Tg2576×PS-1$^{P264L/P264L}$ mice at 2 months had numerous deposits that stained with 4G8 or thioflavine S, indicating that the earliest deposits contained compact, fibrillar amyloid.

In addition to the acceleration in deposition seen in mice, Tg2576×PS-1$^{P264L/P264L}$ another difference was the regional distribution of deposition. Comparing 6-month-old Tg2576×PS-1$^{P264L/P264L}$ mice, 9-month-old Tg2576×PS-1$^{P264L/+}$ mice, and 18-month-old Tg2576 (C57B6/SJL background) mice, the density of deposition was similar in telencephalic structures (data not shown). However, in subcortical structures of the Tg2576×PS-1$^{P264L/P264L}$ mice the amount of Aβ deposition was much greater than in the Tg2576×PS-1$^{P264L/+}$ and Tg2576 mice (data not shown).

Aβ deposition in the APP$^{NLh/NLh}$ mice has been assessed out to 22 months of age. No evidence for deposition was found. Similarly, no deposition was found in PS-1$^{P264L/P264L}$ mice that were wild type for mouse APP at 12 months of age. Extremely rare Aβ deposition was noted in the cortex of APP$^{NLh/NLh}$×PS-1$^{P264L/+}$ mice using both antibody 1153 and thioflavine S at 12 months of age. At 18 months of age Aβ deposits in these mice were more numerous and larger.

Two copies of the PS-1$^{P264L}$ mutation resulted in an increase in Aβ42 in the APP$^{NLh/NLh}$×PS-1$^{P264L/P264L}$ mouse (Table 2) and have resulted in Aβ deposition at an early age. Aβ deposition was not found at 3 months of age but was present at 6 months in APP$^{NLh/NLh}$×PS-1$^{P264L/P264L}$ mice. Deposition increased with age in the APP$^{NLh/NLh}$×PS-1$^{P264L/P264L}$ mice.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A gene-targeted mouse heterozygous for a human Familial Alzheimer's Disease (FAD) mutation comprising a human mutation of the presenilin-1 (PS-1 gene), and a human transgene for Swedish APP695, wherein the Aβ42 protein level is elevated relative to the Aβ42 protein level in a wild-type mouse.

2. A gene-targeted mouse homozygous for a human Familial Alzheimer's Disease (FAD) mutation comprising a human mutation of the presenilin-1 (PS-1 gene), and a human transgene for Swedish APP695, wherein the Aβ42 protein level is elevated relative to the Aβ42 protein level in a wild-type mouse.

3. Generational offspring of the mouse of claim 1 wherein said mutant PS-1 gene is expressed.

4. Generational offspring of the mouse of claim 2 wherein said mutant PS-1 gene is expressed.

5. A method for screening chemical compounds for the ability to decrease in vivo levels of the Aβ peptide, said method comprising the steps of:
   a) administering said chemical compound to the mouse of claim 1; and
   b) measuring the amount of Aβ peptide in a tissue sample from said mouse,
wherein a decrease in the amount of Aβ peptide in said tissue sample is indicative of a chemical compound that has the ability to decrease in vivo levels of said Aβ peptide.

6. A method for screening chemical compounds for the ability to decrease in vivo levels of the Aβ peptide, said method comprising the steps of:
   a) administering said chemical compound to the mouse of claim 2; and
   b) measuring the amount of Aβ peptide in a tissue sample from said mouse,
wherein a decrease in the amount of Aβ peptide in said tissue sample is indicative of a chemical compound that has the ability to decrease in vivo levels of said Aβ peptide.

7. A method for screening chemical compounds for the ability to decrease in vivo levels of the Aβ peptide, said method comprising the steps of:
   a) administering said chemical compound to the mouse of claim 3; and
   b) measuring the amount of Aβ peptide in a tissue sample from said mouse,
wherein a decrease in the amount of Aβ peptide in said tissue sample is indicative of a chemical compound that has the ability to decrease in vivo levels of said Aβ peptide.

8. A method for screening chemical compounds for the ability to decrease in vivo levels of the Aβ peptide, said method comprising the steps of:
   a) administering said chemical compound to the mouse of claim 4; and
   b) measuring the amount of Aβ peptide in a tissue sample from said mouse,
wherein a decrease in the amount of Aβ peptide in said tissue sample is indicative of a chemical compound that has the ability to decrease in vivo levels of said Aβ peptide.

9. The method of claim 5 wherein said tissue sample is selected from the group consisting of brain tissue, non-brain tissue and body fluids.

10. The method of claim 6 wherein said tissue sample is selected from the group consisting of brain tissue, non-brain tissue and body fluids.

11. The method of claim 7 wherein said tissue sample is selected from the group consisting of brain tissue, non-brain tissue and body fluids.

12. The method of claim 8 wherein said tissue sample is selected from the group consisting of brain tissue, non-brain tissue and body fluids.

13. A method for identifying a compound for treating Alzheimer's disease comprising the steps of:
   a) administering a compound to the mouse of claim 1; and
   b) measuring the amount of Aβ peptide in a tissue sample from said mouse,
wherein a decrease in the amount of Aβ peptide in said tissue sample is indicative of a compound that can be used to treat Alzheimer's disease.

14. A method for identifying a compound for treating Alzheimer's disease comprising the steps of:
   a) administering a compound to the mouse of claim 2; and
   b) measuring the amount of Aβ peptide in a tissue sample from said mouse,
wherein a decrease in the amount of Aβ peptide in said tissue sample is indicative of a compound that can be used to treat Alzheimer's disease.

15. A method for identifying a compound for treating Alzheimer's disease comprising the steps of:
   a) administering a compound to the mouse of claim 3; and
   b) measuring the amount of Aβ peptide in a tissue sample from said mouse,
wherein a decrease in the amount of Aβ peptide in said tissue sample is indicative of a compound that can be used to treat Alzheimer's disease.

16. A method for identifying a compound for treating Alzheimer's disease comprising the steps of:
   a) administering a compound to the mouse of claim 4; and
   b) measuring the amount of Aβ peptide in a tissue sample from said mouse,
wherein a decrease in the amount of Aβ peptide in said tissue sample is indicative of a compound that can be used to treat Alzheimer's disease.

17. The method of claim 13 wherein said tissue sample is selected from the group consisting of brain tissue, non-brain tissue and body fluids.

18. The method of claim 14 wherein said tissue sample is selected from the group consisting of brain tissue, non-brain tissue and body fluids.

19. The method of claim 15 wherein said tissue sample is selected from the group consisting of brain tissue, non-brain tissue and body fluids.

20. The method of claim 16 wherein said tissue sample is selected from the group consisting of brain tissue, non-brain tissue and body fluids.

21. A gene-targeted mouse heterozygous for a human presenilin-1 (PS-1) mutation and comprising a human Swedish mutation, said mouse comprising in its genome:
   a DNA sequence encoding a PS-1 protein comprising the human P264L mutation; and
   a DNA sequence encoding a human amyloid precursor protein having the Swedish APP695 mutation;
   wherein the Aβ42 protein level is elevated relative to the Aβ42 protein level in a wild-type mouse.

22. The mouse of claim 21 wherein codon 264 of the PS-1 gene is changed from CCG to CTT, CTC, CTA, CTG, TTA, or TTG.

23. The mouse of claim 22 wherein codon 264 of the PS-1 gene is changed from CCG to CTT.

24. The mouse of claim 21 wherein codon 265 of the PS-1 gene is changed from AAA to AAG.

25. A generational offspring of the mouse of claim 21 wherein said offspring comprises in its genome:
   a DNA sequence encoding a PS-1 protein comprising the human P264L mutation; and
   a DNA sequence encoding a human amyloid precursor protein having the Swedish APP695 mutation;
   wherein the Aβ42 protein level is elevated relative to the Aβ42 protein level in a wild-type mouse.

26. A gene-targeted mouse homozygous for a human presenilin-1 (PS-1) mutation and comprising a human Swedish mutation, said mouse comprising in its genome:
   a DNA sequence encoding a PS-1 protein comprising the human P264L mutation; and
   a DNA sequence encoding a human amyloid precursor protein having the Swedish APP695 mutation;
   wherein the Aβ42 protein level is elevated relative to the Aβ42 protein level in a wild-type mouse.

27. The mouse of claim 26 wherein codon 264 of the PS-1 gene is changed from CCG to CTT, CTC, CTA, CTG, TTA, or TTG.

28. The mouse of claim 27 wherein codon 264 of the PS-1 gene is changed from CCG to CTT.

29. The mouse of claim 26 wherein codon 265 of the PS-1 gene is changed from AAA to AAG.

30. A generational offspring of the mouse of claim 26 wherein said offspring comprises in its genome:
   a DNA sequence encoding a PS-1 protein comprising the human P264L mutation; and
   a DNA sequence encoding a human amyloid precursor protein having the Swedish APP695 mutation;
   wherein the Aβ42 protein level is elevated relative to the Aβ42 protein level in a wild-type mouse.

31. A method for screening a compound for the ability to decrease in vivo levels of the Aβ peptide comprising the steps of:
   administering said compound to the mouse of claim 21; and
   measuring the amount of Aβ peptide in a tissue sample from said mouse;
   wherein a decrease in the amount of Aβ peptide in said tissue sample is indicative of a compound that has the ability to decrease in vivo levels of said Aβ peptide.

32. A method for screening a compound for the ability to decrease in vivo levels of the Aβ peptide comprising the steps of:
   administering said compound to the mouse of claim 25; and
   measuring the amount of Aβ peptide in a tissue sample from said mouse;
   wherein a decrease in the amount of Aβ peptide in said tissue sample is indicative of a compound that has the ability to decrease in vivo levels of said Aβ peptide.

33. A method for screening a compound for the ability to decrease in vivo levels of the Aβ peptide comprising the steps of:
   administering said compound to the mouse of claim 26; and
   measuring the amount of Aβ peptide in a tissue sample from said mouse;
   wherein a decrease in the amount of Aβ peptide in said tissue sample is indicative of a compound that has the ability to decrease in vivo levels of said Aβ peptide.

34. A method for screening a compound for the ability to decrease in vivo levels of the Aβ peptide comprising the steps of:

administering said compound to the mouse of claim 30; and measuring the amount of Aβ peptide in a tissue sample from said mouse;

wherein a decrease in the amount of Aβ peptide in said tissue sample is indicative of a compound that has the ability to decrease in vivo levels of said Aβ peptide.

35. The method of claim 31 wherein said tissue sample is brain tissue, non-brain tissue, or a body fluid.

36. The method of claim 32 wherein said tissue sample is brain tissue, non-brain tissue, or a body fluid.

37. The method of claim 33 wherein said tissue sample is brain tissue, non-brain tissue, or a body fluid.

38. The method of claim 34 wherein said tissue sample is brain tissue, non-brain tissue, or a body fluid.

39. The mouse of claim 1 wherein said human mutation of the PS-1 gene is A79V, V82L, V96F, Y115C, E120D, E120K, M139I, M139T, M139V, I143F, I143T, M146I, M146L (A→T), H163Y, G209V, A231T, A231V, M233T, L235P, L250S, A260V, L262F, C263R, P264L, P267S, R269H, R278T, E280A, E280G, A285V, E318G, G378E, G384A, L392V, M146L (A→C), M146V, H163R, I213T, L286V, A246E, Y115H, T116N, P117L, L171P, E123L, N135D, C410Y, A426P, P436S, M139K, T147I, W165C, L173W, S390I, L166R, S169L, P436Q, S169P, E184D, G209R, L219P, M233L, A409T, E273A, L282R, G378A, N405S, A409T, L424R, a Δ exon 9 splice acceptor site deletion mutation (G→T with S290C), a Δ exon 9 splice acceptor site deletion mutation (G→A with S290C), a Δ exon 9 Finn 4,555 basepair deletion, a Δ intron 4 splice donor consensus sequence G deletion, a C→T mutation at position-48 in the 5' promoter, a C→G mutation at position-280 in the 5' promoter, or a A→G mutation at position-2818 in the 5' promoter.

40. The mouse of claim 2 wherein said human mutation of the PS-1 gene is A79V, V82L, V96F, Y115C, E120D, E120K, M139I, M139T, M139V, I143F, I143T, M146I, M146L (A→T), H163Y, G209V, A231T, A231V, M233T, L235P, L250S, A260V, L262F, C263R, P264L, P267S, R269H, R278T, E280A, E280G, A285V, E318G, G378E, G384A, L392V, M146L (A→C), M146V, H163R, I213T, L286V, A246E, Y115H, T116N, P117L, L171P, E123L, N135D, C410Y, A426P, P436S, M139K, T147I, W165C, L173W, S390I, L166R, S169L, P436Q, S169P, E184D, G209R, L219P, M233L, A409T, E273A, L282R, G378A, N405S, A409T, L424R, a Δ exon 9 splice acceptor site deletion mutation (G→T with S290C), a Δ exon 9 splice acceptor site deletion mutation (G→A with S290C), a Δ exon 9 Finn 4,555 basepair deletion, a Δ intron 4 splice donor consensus sequence G deletion, a C→T mutation at position-48 in the 5' promoter, a C→G mutation at position-280 in the 5' promoter, or a A→G mutation at position-2818 in the 5' promoter.

* * * * *

SEQUENCE LISTING

<160> NUMBER OF SEQ ID NOS: 17

<210> SEQ ID NO 1
<211> LENGTH: 21
<212> TYPE: DNA
<213> ORGANISM: Artificial Sequence

```
<220> FEATURE:
<223> OTHER INFORMATION: Oligonucleotide Primer

<400> SEQUENCE: 1
ctcatcttgg ctgtgatttc a                                                 21

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 2
gttgtgttcc agtctcca                                                     18

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 3
atttagtggc tgttttgtg                                                    19

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 4
aggagtaaat gagagctgga                                                   20

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 5
tgaaatcaca gccaagatga g                                                 21

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 6
gcactcctga tctggaattt tg                                                22

<210> SEQ ID NO 7
<211> LENGTH: 48
<212> TYPE: DNA
<213> ORGANISM: Artificial Sequence
<220> FEATURE:
<223> OTHER INFORMATION: Oligonucleotide Primer

<400> SEQUENCE: 7
ggaaagaatg cggccgctgt cgacgttaac atgcatataa cttcgtat                    48
```

<210> SEQ ID NO 8
<211> LENGTH: 47
<212> TYPE: DNA
<213> ORGANISM: Artificial Sequence
<220> FEATURE:
<223> OTHER INFORMATION: Oligonucleotide Primer

<400> SEQUENCE: 8
gctctcgaga taacttcgta tagcatacat tatacgaagt tatatgc           47

<210> SEQ ID NO 9
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 9
cgttctagaa taacttcgta taatgtatgc tat           33

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 10
cgtggatcca taacttcgta tagcatacat tat           33

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 11
ttgtgtctta agggtccgct tcgtatg           27

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 12
cggaccctta agacacaaaa cagccac           27

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 13
ggattgcacg caggttctcc           20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide Primer

```
<400> SEQUENCE: 14
ccggcttcca tccgagtacg                                              20

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 15
cccgtggagg aggtcagaag tcag                                         24

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 16
ttacgggttg agccatgaat g                                            21

<210> SEQ ID NO 17
<211> LENGTH: 16
<212> TYPE: PRT
<213> ORGANISM: Homo sapiens

<400> SEQUENCE: 17

Glu Gly Asp Pro Glu Ala Gln Arg Arg Val Ser Lys Asn Ser Lys Tyr
1               5                   10                  15
```